US012730115B2

(12) United States Patent
Kim et al.

(10) Patent No.: US 12,730,115 B2
(45) Date of Patent: Sep. 8, 2026

(54) DETECTION OF BETA AMYLOID PROTEIN AS ALZHEIMER'S DISEASE-CAUSING FACTOR IN PALATINE TONSIL AND USE THEREOF

(71) Applicant: THE CATHOLIC UNIVERSITY OF KOREA INDUSTRY-ACADEMIC COOPERATION FOUNDATION, Seoul (KR)

(72) Inventors: Sung Won Kim, Seoul (KR); Jung Ho Chun, Seoul (KR); Il Hwan Lee, Gyeonggi-do (KR); Jung Yeon Lim, Seoul (KR); Do Hyun Kim, Seoul (KR); Seung Ho Yang, Seoul (KR); Jung Eun Lee, Gyeonggi-do (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 615 days.

(21) Appl. No.: 18/310,708

(22) Filed: May 2, 2023

(65) Prior Publication Data

US 2024/0329057 A1 Oct. 3, 2024

Related U.S. Application Data

(63) Continuation-in-part of application No. PCT/KR2021/015751, filed on Nov. 3, 2021.

(30) Foreign Application Priority Data

Nov. 3, 2020 (KR) ........................ 10-2020-0144932
Oct. 28, 2021 (KR) ........................ 10-2021-0145842

(51) Int. Cl.
*G01N 33/68* (2006.01)
*G01N 33/569* (2006.01)

(52) U.S. Cl.
CPC ... *G01N 33/6896* (2013.01); *G01N 33/56938* (2013.01); *G01N 2474/20* (2021.08); *G01N 2800/2821* (2013.01)

(58) Field of Classification Search
CPC ......... G01N 33/6893; G01N 2333/765; G01N 2800/347
See application file for complete search history.

(56) References Cited

U.S. PATENT DOCUMENTS

2019/0120859 A1* 4/2019 Lee ..................... G01N 33/542

FOREIGN PATENT DOCUMENTS

KR 20150144283 12/2015

OTHER PUBLICATIONS

Allen, H. B., et al., "Psoriasis, Chronic Tonsillitis, and Biofilms: Tonsillar Pathologic Findings Supporting a Microbial Hypothesis", Ear, Nose, and Throat Journal, vol. 97, No. 3 (2018), pp. 79-82.

(Continued)

*Primary Examiner* — Dennis White
(74) *Attorney, Agent, or Firm* — Riverside Law LLP

(57) ABSTRACT

The present disclosure relates to the detection of beta amyloid protein as an Alzheimer's disease-causing factor in the palatine tonsil and a use thereof and, more specifically, to the diagnosis of Alzheimer's disease by identifying the expression of beta amyloid and/or *Staphylococcus aureus* in a tonsillar sample. The present disclosure can diagnose Alzheimer's disease through the expression of beta amyloid and/or *Staphylococcus aureus* in a palatine tonsil tissue and, furthermore, can be very advantageously used for revealing the pathogenesis of Alzheimer's disease and for treating Alzheimer's disease.

10 Claims, 25 Drawing Sheets

(56) References Cited

OTHER PUBLICATIONS

Kheirandish-Gozal, L, et al., "Biomarkers of Alzheimer Disease in Children with Obstructive Sleep Apnea: Effect of Adenotonsillectomy", Sleep, vol. 39, No. 6 (2016), pp. 1225-1232.
Olsen, i., et al., "Can oral infection be a risk factor for Alzheimer's disease?", Journal of Oral Microbiology, vol. 7, No. 1 (2015), Article 29143.
Salinas N., et al., "Extreme amyloid polymorphism in *Staphylococcus aureus* virulent PSMα peptides", Nature Communications, vol. 9, No. 1 (2018), Article 3512.

* cited by examiner

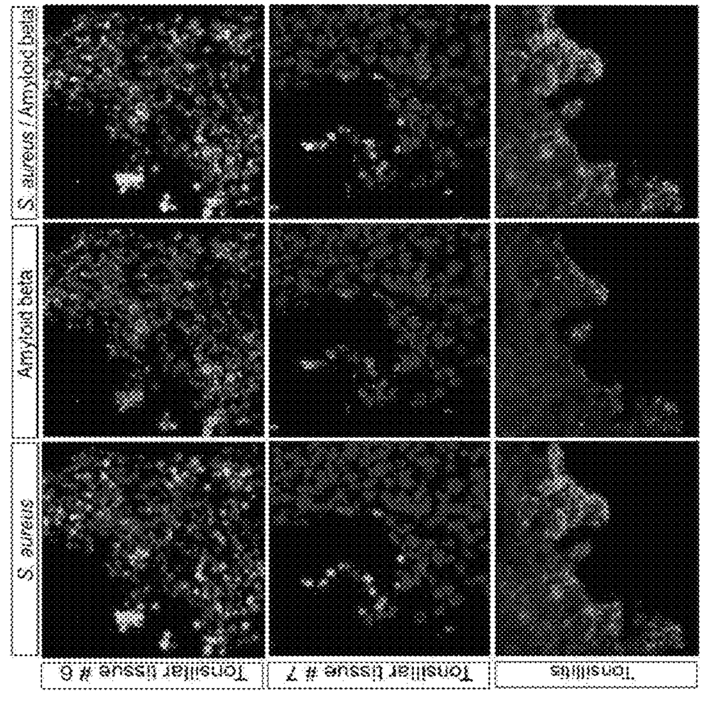
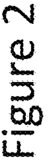
Fig. 2A
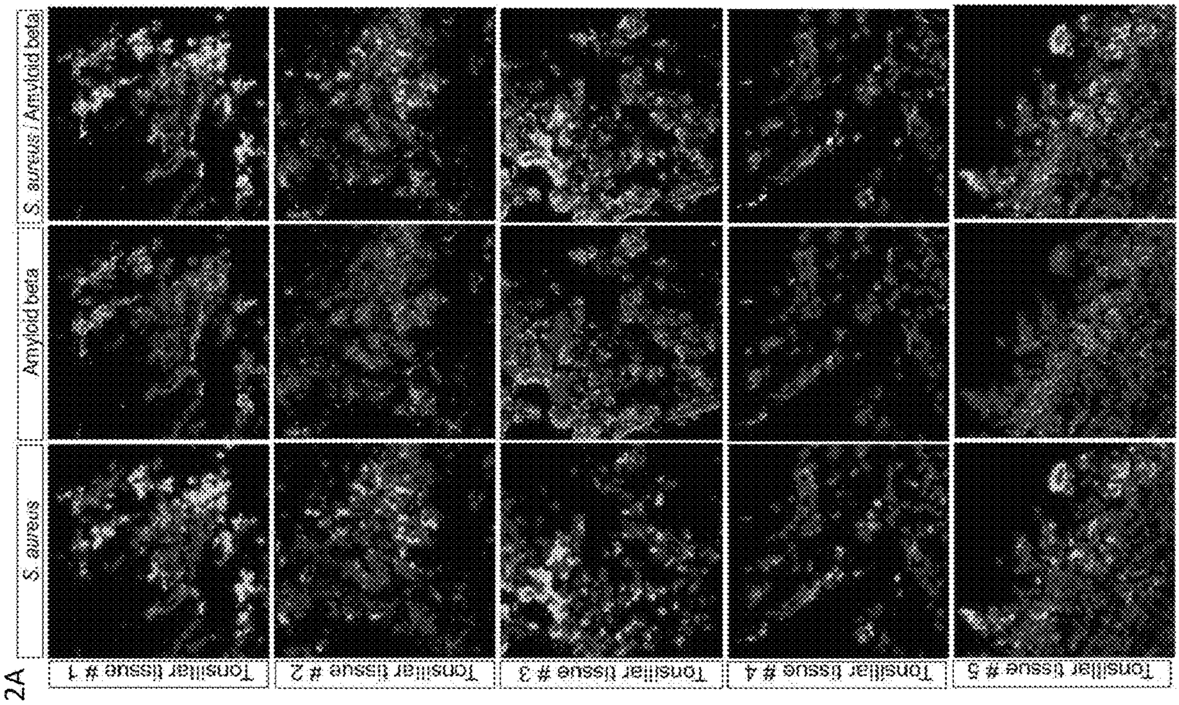

Aβ (15kDa)

β-actin

CD 4 (helper T cells)

Fig. 4I
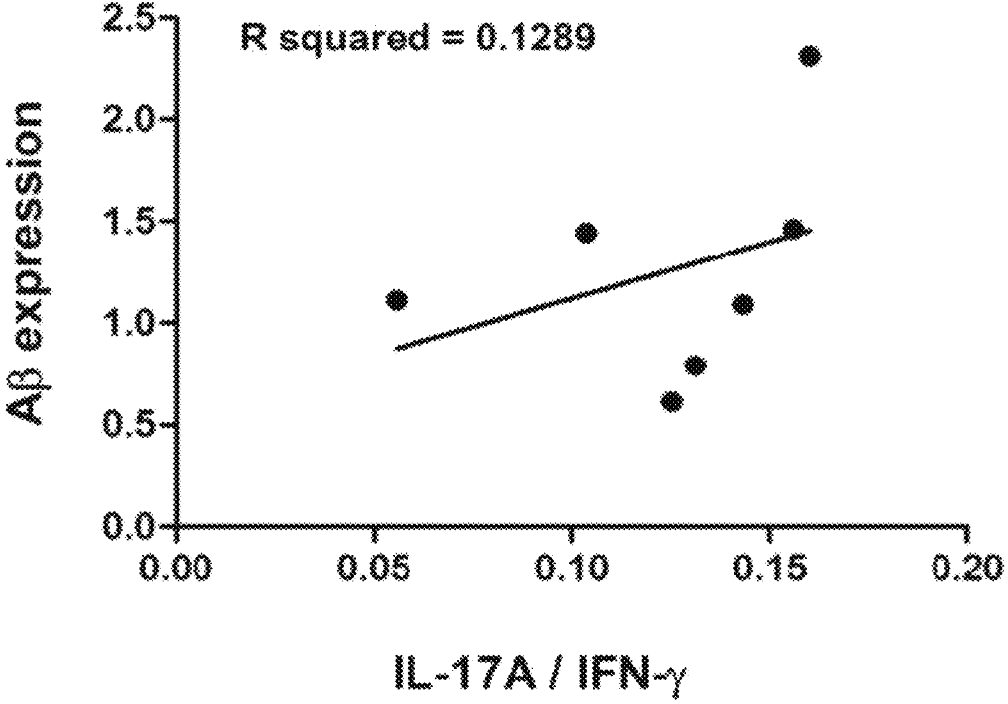
Fig. 4J
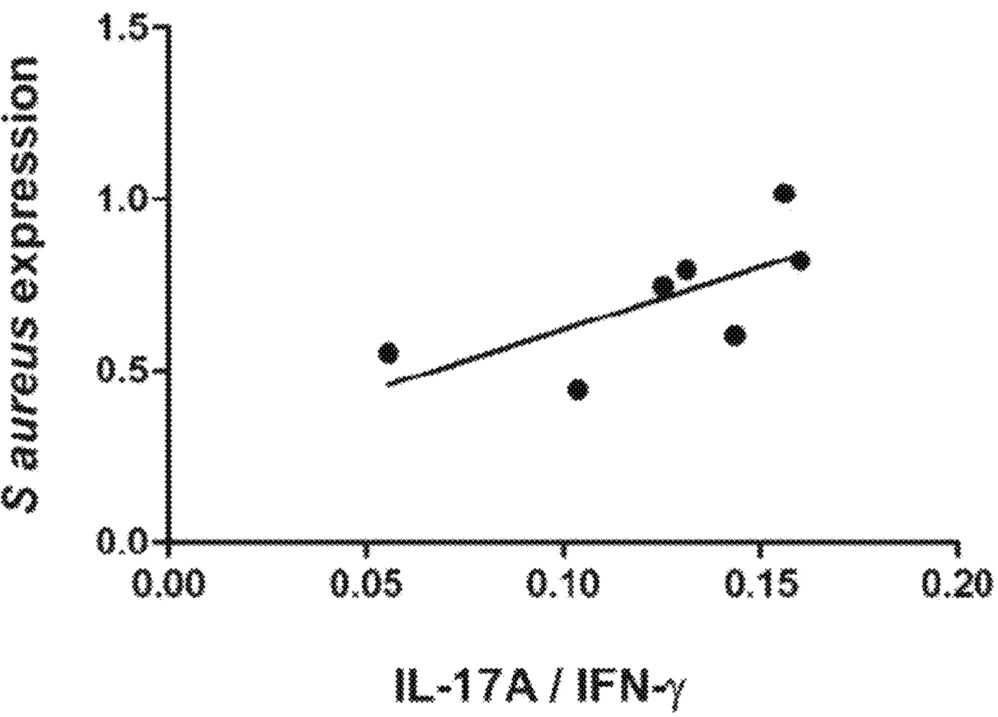
Figure 4 Cont.

DETECTION OF BETA AMYLOID PROTEIN AS ALZHEIMER'S DISEASE-CAUSING FACTOR IN PALATINE TONSIL AND USE THEREOF

CROSS-REFERENCE TO RELATED APPLICATIONS

This application is a continuation-in-part of International Patent Application No. PCT/KR2021/015751, filed Nov. 3, 2021, which claims priority to Korean Patent Application No. 10-2020-0144932, filed Nov. 3, 2020, and Korean Patent Application No. 10-2021-0145842, filed Oct. 28, 2021, the contents of each of which are hereby incorporated by reference in their entirety.

TECHNICAL FIELD

The present disclosure relates to the detection of beta amyloid protein as an Alzheimer's disease-causing factor in the palatine tonsil and a use thereof and, more specifically, to the diagnosis of Alzheimer's disease by identifying the expression of beta amyloid and/or *Staphylococcus aureus* in a tonsillar sample.

BACKGROUND ART

A degenerative brain disease refers to one of the degenerative diseases that develop in the brain with advancing years. It is known that the degenerative brain disease is caused by a decrease in the number of brain cells due to which certain brain cell groups in the brain and spinal cord gradually lose their functions for reasons unknown to date, death of the brain nerve cells, which are most important for the transmission of information in the brain nervous system, problems in the formation or function of synapses that transmit information between brain nerve cells, and abnormal symptoms or reduction in electrical activity of the cranial nerves. The nerve cells of the brain and spinal cord have a wide variety of functions depending on their location, and thus show a great variety of clinical aspects depending on which location the nerve cells are first damaged and lose functioning and depending on what form such dysfunction progresses.

The degenerative brain disease may be classified by considering the main symptoms and the affected brain regions, and examples thereof comprise Alzheimer's disease, Parkinson's disease, Huntington's disease, multiple sclerosis, and amyotrophic lateral sclerosis (ALS) (also known as Lou Gehrig's disease).

Dementia is a disease that mainly affects the elderly and is a geriatric disease whose prevalence increases dramatically with age. In the United States, it is currently reported that there are about 2 million dementia patients. Similarly in Korea, the number of people with dementia has increased from about 280,000 people, or 8.2% of the elderly aged 65 or older, in 2000 to about 360,000 people, or 8.3%, in 2005. Causes of dementia comprise atrophic changes in the brain, cerebrovascular disorders, inflammatory disorders in the brain, metabolic and endocrine diseases such as korsakoff syndrome, tumors, trauma, and addiction, among which senile dementia (Alzheimer's disease, AD) caused by the atrophic changes in the brain accounts for the highest rate.

The pathologic characteristic of Alzheimer's Disease (AD) is the neurofibrillary tangle (NFT), which appears as a result of the aggregation of hyperphosphorylated tau protein in the cerebral cortex and hippocampus, and senile plaques, the main components of which are amyloid beta proteins (amyloid beta peptide Aβ) accumulated outside nerve cells. It is known that Aβ protein destroys nerve cells in cerebral parts and the cerebral cortex that make acetylcholine, a neurotransmitter, thus reducing the activation state of acetylcholine and generating reactive oxygen species (ROS) to cause oxidative damage and nerve cell death. In addition, mechanisms related to inflammation as well as oxidative cell death are the main causes of brain cell damage.

Biomarkers used for early diagnosis of Alzheimer's disease comprise brain magnetic resonance imaging, brain positron emission tomography (evaluation of glucose metabolism or amyloid and tau accumulation), and cerebrospinal fluid examination (measurement of amyloid and tau concentration). These examinations have limitations in that they are very expensive or may only be performed in some large hospitals, and that they are invasive and psychologically repulsive like the cerebrospinal fluid examination. In this regard, when there is a method that may be tested using tonsil tissue, which is a simple sample, in order to predict the possibility of developing Alzheimer's disease at an early stage, it will be very useful especially in screening tests targeting a large number of elderly people in the community. However, there is no reliable method to check the Alzheimer's disease in the tonsils yet.

DISCLOSURE

Technical Problem

Accordingly, the present inventors completed the present disclosure by confirming that Alzheimer's disease may be diagnosed and prevented at an early stage by confirming the expression or accumulation of beta amyloid and *Staphylococcus aureus* strains in the palatine tonsil.

Accordingly, an aspect of the present disclosure is to provide a method for providing information needed to predict an onset of Alzheimer's disease, wherein the method comprises: a) measuring an expression level or plaque accumulation level of beta amyloid in a tonsillar sample obtained from a subject; and b) determining that the higher the expression level or plaque accumulation level of beta amyloid in the stage a) is compared to an expression amount of normal people, the higher the risk of developing the Alzheimer's disease.

Another aspect of the present disclosure is to provide a method for providing information needed to select a tonsillectomy target, wherein the method comprises: a) measuring an expression amount or accumulation amount of beta amyloid in a tonsillar sample derived from a subject; and b) determining the tonsillectomy target when an expression level or plaque accumulation level of beta amyloid in the stage a) is higher than an expression amount of normal people.

However, technical tasks to be achieved by the present disclosure are not limited to the aforementioned tasks, and other tasks, which are not mentioned herein, will be clearly understood from the following description by those skilled in the art.

Technical Solution

An embodiment of the present disclosure provides a method for providing information needed to predict an onset of Alzheimer's disease, wherein the method comprises: a)

measuring an expression level or plaque accumulation level of beta amyloid in a tonsillar sample obtained from a subject; and b) determining that the higher the expression level or plaque accumulation level of beta amyloid in the stage a) is compared to an expression amount of normal people, the higher the risk of developing the Alzheimer's disease.

In addition, an embodiment of the present disclosure provides a method for providing information needed to predict an onset of Alzheimer's disease, wherein the method comprises:

a) measuring an expression level of *Staphylococcus aureus* strains in a tonsillar sample obtained from a subject; and b) determining that the higher the expression level of *Staphylococcus aureus* in the stage a) is compared to an expression amount of normal people, the higher the risk of developing the Alzheimer's disease.

In addition, an embodiment of the present disclosure provides a method for predicting a risk of developing Alzheimer's disease, wherein the method comprises: a) measuring an expression level of *Staphylococcus aureus* strains in a tonsillar sample obtained from a subject; and b) determining that the higher the expression level of *Staphylococcus aureus* in the stage a) is compared to an expression amount of normal people, the higher the risk of developing the Alzheimer's disease.

In addition, an embodiment of the present disclosure provides a method for providing information needed to select a tonsillectomy target, wherein the method comprises: a) measuring an expression amount or accumulation amount of beta amyloid in a tonsillar sample derived from a subject; and b) determining that the subject is a target for tonsillectomy when an expression level or plaque accumulation level of beta amyloid in the stage a) is higher than an expression amount of normal people.

In addition, an embodiment of the present disclosure provides a method for predicting a risk of developing Alzheimer's disease, wherein the method comprises: a) measuring an expression amount or accumulation amount of beta amyloid in a tonsillar sample derived from a subject; and b) determining that the subject has Alzheimer's disease when an expression level or plaque accumulation level of beta amyloid in the stage a) is higher than an expression amount of normal people.

In addition, an embodiment of the present disclosure provides a method for providing information needed to prevent Alzheimer's disease, wherein the method comprises: a) measuring an expression amount or accumulation amount of beta amyloid in a tonsillar sample derived from a subject; and b) determining that the subject is a target for tonsillectomy when an expression level or plaque accumulation level of beta amyloid in the stage a) is higher than an expression amount of normal people.

In an embodiment of the present disclosure, a method for measuring the expression level, may be one or more selected from the group consisting of Western blotting, an ELISA, a radioimmunoassay, radioimmunodiffusion, Ouchterlony immunodiffusion, rocket immunoelectrophoresis, immunohistostaining, an immunoprecipitation assay, a complement fixation assay, FACS, and a protein chip assay, but is not limited thereto.

In another embodiment of the present disclosure, the stage a) may further comprise measuring an expression level of *Staphylococcus aureus* strains, but is not limited thereto.

In yet another embodiment of the present disclosure, the beta amyloid in the stage a) may colocalize with *Staphylococcus aureus*, but is not limited thereto.

In yet another embodiment of the present disclosure, the subject may be a patient with a tonsil-related disease, but is not limited thereto.

In yet another embodiment of the present disclosure, the tonsil-related disease may be tonsillitis or enlarged tonsils, but is not limited thereto.

In yet another embodiment of the present disclosure, the tonsillar sample may be tonsil tissue or tonsillar stone, but is not limited thereto.

In addition, an embodiment of the present disclosure provides a composition for predicting a risk of developing Alzheimer's disease, wherein the composition comprises one or more selected from the group consisting of: a substance for detecting an expression amount of beta amyloid protein or an accumulation amount thereof; and a substance for detecting an expression amount of *Staphylococcus aureus*, and wherein the composition uses tonsils as a sample.

In addition, an embodiment of the present disclosure provides a use of a composition for predicting a risk of developing Alzheimer's disease, wherein the composition comprises one or more selected from the group consisting of: a substance for detecting an expression amount of beta amyloid protein or an accumulation amount thereof, and a substance for detecting an expression amount of *Staphylococcus aureus*, and wherein the composition uses tonsils as a sample.

In addition, an embodiment of the present disclosure provides a use of a composition for preparing an agent for predicting a risk of developing Alzheimer's disease, wherein the composition comprises one or more selected from the group consisting of: a substance for detecting an expression amount of beta amyloid protein or an accumulation amount thereof, and a substance for detecting an expression amount of *Staphylococcus aureus*, and wherein the composition uses tonsils as a sample.

In addition, an embodiment of the present disclosure provides a kit for predicting a risk of developing Alzheimer's disease, wherein the kit comprises the composition.

Advantageous Effects

An embodiment of the present disclosure can diagnose Alzheimer's disease through the expression of beta amyloid and/or *Staphylococcus aureus* in a palatine tonsil tissue and, furthermore, can be very advantageously used for revealing the pathogenesis of Alzheimer's disease and for treating Alzheimer's disease.

DESCRIPTION OF DRAWINGS

FIGS. 4A to 4J are diagrams identifying the expression relationship between IL-17A and IFN-γ expressing T cells and beta amyloid that regulate immune responses in seven different tonsil tissues obtained through tonsillectomy or the expression relationship between IL-17A and IFN-γ expressing T cells and *Staphylococcus aureus* (*S. aureus*).

FIGS. 6A and 6B identify the expression of beta amyloid in normal organoids and *Staphylococcus aureus* (*S. aureus*)-treated organoids. FIGS. 6C and 6D identify the expression of neural cell markers Nestin and Iba-1 in normal organoids and *Staphylococcus aureus* (*S. aureus*)-treated organoids. FIG. 6E is the result of H&E staining of normal organoids and *Staphylococcus aureus* (*S. aureus*)-treated organoids. FIG. 6F shows the level of beta amyloid-positive expressing cells in normal organoids and *Staphylococcus aureus* (*S. aureus*)-treated organoids. The rightmost scale bar in FIGS. 6A to 6D represents 20 μm, and the remaining scale bars represent 50 μm. The scale bar in FIG. 6E represents 500 μm.

BEST MODE FOR DISCLOSURE

Figure 1:
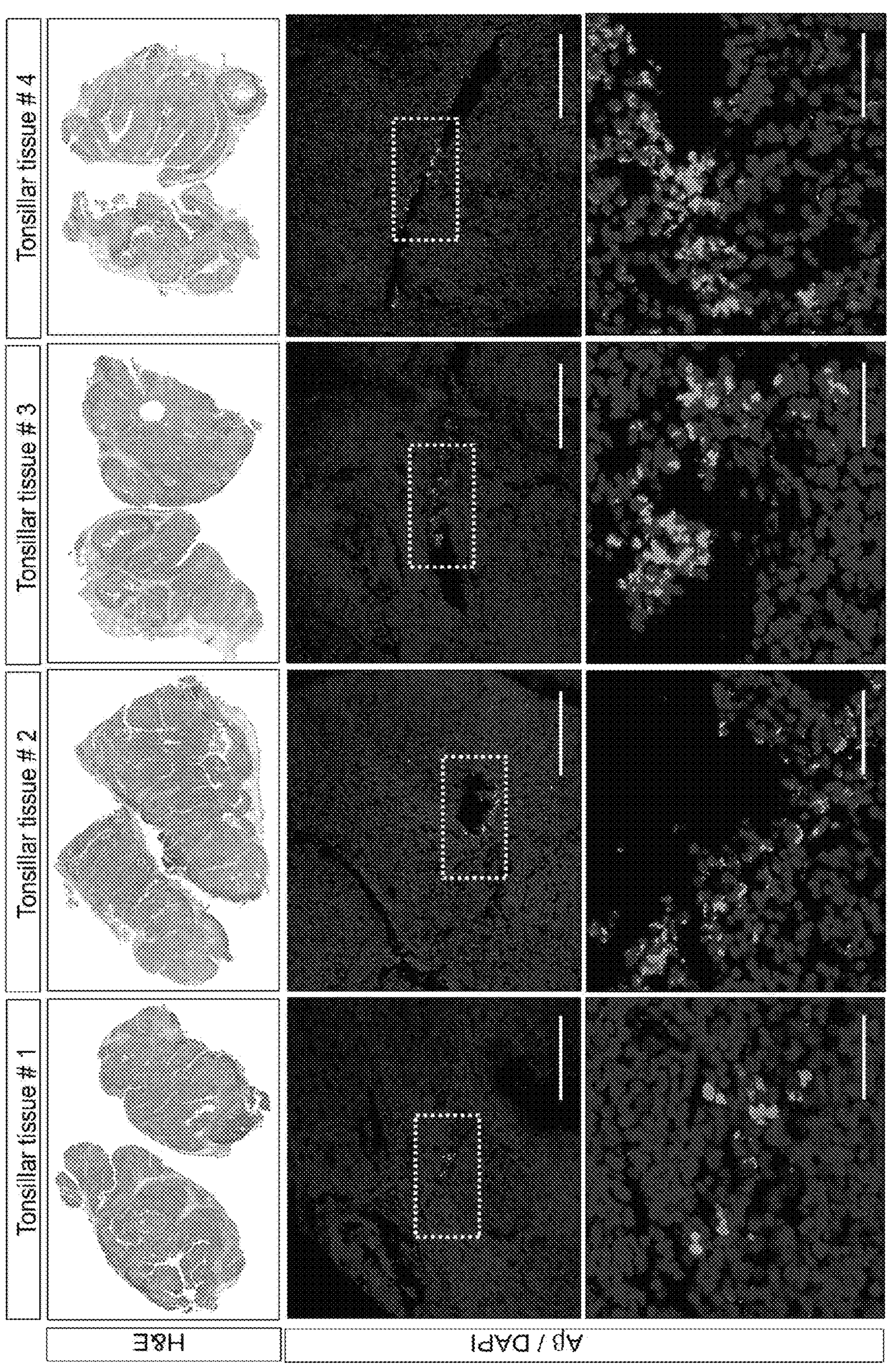
FIG. 1 shows the results of identifying the expression of beta amyloid using immunofluorescence staining in tonsil tissue obtained through tonsillectomy.

An embodiment of the present disclosure provides a method for providing information needed to predict an onset of Alzheimer's disease, wherein the method comprises: a) measuring an expression level or plaque accumulation level of beta amyloid in a tonsillar sample obtained from a subject; and b) determining that the higher the expression level or plaque accumulation level of beta amyloid in the stage a) is compared to an expression amount of normal people, the higher the risk of developing the Alzheimer's disease.

In addition, an embodiment of the present disclosure provides a method for providing information needed to select a tonsillectomy target, wherein the method comprises: a) measuring an expression amount or accumulation amount of beta amyloid in a tonsillar sample derived from a subject; and b) determining the tonsillectomy target when an expression level or plaque accumulation level of beta amyloid in the stage a) is higher than an expression amount of normal people.

In addition, an embodiment of the present disclosure provides a method for providing information needed to predict an onset of Alzheimer's disease, wherein the method comprises:

a) measuring an expression level of *Staphylococcus aureus* strains in a tonsillar sample obtained from a subject; and b) determining that the higher the expression level of *Staphylococcus aureus* in the stage a) is compared to an expression amount of normal people, the higher the risk of developing the Alzheimer's disease.

Hereinafter, an embodiment of the present disclosure will be described in detail.

In an embodiment of the present disclosure, beta amyloid (P amyloid) is one of the main pathological features of Alzheimer's disease and is a major component of extracellular neuronal plaques. In an embodiment of the present disclosure, the beta amyloid may be a beta amyloid oligomer of 15 kDa, but is not limited thereto.

In an embodiment of the present disclosure, *Staphylococcus aureus* is a gram-positive, facultatively aerobic, clump-forming cocci bacteria that commonly colonizes in the nose and on the skin of healthy humans. Approximately 20-30% of the population is colonized with *S. aureus* at any given time. *Staphylococcus aureus* bacteria, sometimes also referred to as "staph", "Staph. *aureus*," or "*S. aureus*," are considered opportunistic pathogens that cause minor infections (e.g., pimples, boils) and systemic infections.

To date, detection of the accumulation of beta amyloid plaques has been identified by post-mortem brain biopsies of Alzheimer's dementia patients and identified Alzheimer's dementia. Recently, technologies such as PIB-PET, which may check the accumulation of brain amyloid beta by brain imaging, have been developed, but this is a very expensive test and expensive equipment that may only be performed at some university hospitals, and it causes many inconveniences to patients. Accordingly, the method according to an embodiment of the present disclosure, which may simply identify Alzheimer's disease by detecting beta amyloid and/or *Staphylococcus aureus* in tonsillar samples, is very important.

In an embodiment of the present disclosure, the tonsillar sample may be tonsil tissue or tonsillar stone, but is not limited thereto.

In an embodiment of the present disclosure, tonsillar stones refer to yellow grains formed by accumulation of fragments of epithelial tissues in the tonsils and tonsils. In the case of using tonsillar stones as a sample, it is expected that Alzheimer's disease may be easily identified because the tonsillar stone may be easily collected from the tonsils without anesthesia, resection, or surgery.

Accumulation of amyloid beta in the brain begins 15-20 years before clinical symptoms such as dementia and forgetfulness appear. In patients with no clinical symptoms or mild clinical symptoms, tonsil biopsy may be used to diagnose Alzheimer's disease early, as well as to offer a chance to slow or prevent its progression at an early stage. In addition, since an Alzheimer's disease patient in which amyloid beta has not accumulated in the brain may be identified, a treatment strategy for such a patient may be different.

Accordingly, the stage a) may further comprise measuring an expression level of *Staphylococcus aureus*, but is not limited thereto.

In addition, the beta amyloid in the stage a) may colocalize with *Staphylococcus aureus*, but is not limited thereto.

In an embodiment of the present disclosure, after collecting human palatine tonsil tissues through tonsillectomy, the expression levels of beta amyloid and/or *Staphylococcus aureus* were identified (Examples 1 and 2), and *Staphylo-*

*coccus aureus* strains were identified to colocalize around or inside beta amyloid plaques (Example 2).

In addition, with the increase of age, mucosal glands decrease due to atrophy (aging process) of the mucous membrane of the upper respiratory tract, especially the nose. As a result, about 1 liter of nasal mucus automatically flows toward the nasopharynx to clean germs, viruses, molds, etc. in the nose, thereby also significantly reducing the mucociliary clearance to maintain a constant flora. Decreased mucociliary clearance may result in ascending infection that reverses the flow of mucus from pathogens in the upper respiratory tract, particularly in the palatine tonsils of persons with enlarged tonsils. Accordingly, the frequency of *Staphylococcus aureus* was highest in the periolfactory pathway (the space around the olfactory nerve that goes to the cribriformplate) or the peritrigeminal pathway (the passage around the sensory nerve branches) through the olfactory mucosal epithelium. In other words, the present inventors first proved this hypothesis that an inflammatory response occurs due to brain infection by *Staphylococcus aureus* and a degenerative brain disease occurs due to the accumulation of beta amyloid protein, a by-product of this inflammatory process.

As used herein, the term "polypeptide" is used interchangeably herein with the terms "polypeptides" and "protein(s)", and refers to a polymer of amino acid residues, e.g., as typically found in proteins in nature.

As used herein, the term "detection" is meant to encompass all of a measurement and identification of the presence (expression) or absence of a target substance (a marker protein, MRS, or/and CK19 in the present disclosure), or a measurement and identification of a change in presence level (expression level) of a target substance. In the same context, measuring the expression level of the protein means measuring the expression or non-expression (that is, measuring the presence or absence of expression) or measuring the level of qualitative or quantitative change of the protein. The measurement may be carried out without limitation, comprising all qualitative methods (analyses) and quantitative methods. In the measurement at the protein level, the kinds of qualitative and quantitative methods are well known in the art, and the test methods described herein are comprised therein. Specific comparisons of the protein level for respective methods are well known in the art. Accordingly, the detection of a target protein is meant to encompass detecting the presence or absence of the target protein or identifying the increase in expression level (up-regulation) of the protein.

As used herein, the term "increase in expression (or high expression)" of a protein means that a previously unexpressed one is expressed (that is, a previously undetected one is detected) or an overexpression is relatively shown relative to a normal level (that is, the detected amount is increased). It may be understood by a person skilled in the art that the meaning of the term opposite thereto has an opposite meaning on the basis of the definition.

As used herein, the term "probe" refers to a fragment of a polynucleotide, such as RNA or DNA, capable of specifically binding to mRNA or complementary DNA (cDNA) of a specific gene and having a length of from several to several hundreds of base pairs. The probe is labeled to check the presence or absence of target mRNA or cDNA to be bound or the expression level thereof. For the purpose of an embodiment of the present disclosure, the probe complementary to mRNA of a target protein is subjected to hybridization with a sample of a subject to measure an expression amount of the mRNA of the target protein, which may be used for maternal abnormalities such as fatty acid movement or preeclampsia in the placenta and embryonic tissues. The selection and hybridization of the probe may be properly selected according to the technique known in the art. The primers or probes of an embodiment of the present disclosure may be chemically synthesized using a phosphoramidite solid-phase synthesis method or another well-known method. In addition, the primers or probes may be variously modified by a method known in the art within the scope in which the hybridization with the mRNA of the target protein is not disturbed. Examples of the modification are methylation, capping, substitution of at least one natural nucleotide with an analogue thereof, and modification between nucleotides, for example, modification with an uncharged linker (for example, methyl phosphonate, phosphotriester, phosphoroamidate, and carbamate) or a charged linker (for example, phosphorothioate, and phosphorodithioate), binding with a labeling material using fluorescence or enzyme, and the like.

As used herein, the term "antibody" refers to a specific protein molecule directed against an antigenic region. The antibody used in an embodiment of the present disclosure may be a monoclonal or polyclonal antibody, an immunologically active fragment (for example, a Fab or (Fab)2 fragment), an antibody heavy chain, a humanized antibody, an antibody light chain, a genetically manipulated single-chain Fv molecule, or a chimeric antibody. For example, polyclonal antibodies may be produced by a method of injecting the biomarker protein antigen of an embodiment of the present disclosure into an animal and collecting blood from the animal to obtain a serum comprising antibodies. Such antibodies may be prepared using a variety of warm-blooded animals such as horses, cows, goats, sheep, dogs, chickens, turkeys, rabbits, mice, or rats.

Monoclonal antibodies may also be prepared by a fusion method widely known in the art (Kohler and Milstein, European J. of Immunol., 6:511-519 (1976)), a recombinant DNA method (U.S. Pat. No. 4,816,567), and a phage antibody library technique (Clackson et al, Nature, 352:624-628 (1991); and Marks et al, J. Mol. Biol., 222:58, 1-597 (1991)).

As used herein, the term "aptamer" refers to a material capable of specifically binding to an analyte to be detected in a sample, and a single-stranded nucleic acid having a stable tertiary structure by itself (DNA, RNA, or a modified nucleic acid), and may specifically confirm the presence of a target protein in a sample. By a general method of preparing an aptamer, an aptamer may be synthesized by determining the sequence of an oligonucleotide with selective and high binding ability to a target protein to be confirmed, and by modifying it with —SH, —COOH, —OH, or NH2 to make the 5' or 3' end of the oligonucleotide bind to a functional group of an aptamer chip, but an embodiment of the present disclosure is not limited thereto.

In an embodiment of the present disclosure, the term "diagnosing Alzheimer's disease" means determining whether a patient has a possibility of developing Alzheimer's disease, a relatively high possibility of developing Alzheimer's disease, or whether Alzheimer's disease has already occurred. The method of an embodiment of the present disclosure may be used to delay the onset or prevent the onset of Alzheimer's disease through special and appropriate management for any specific patient with a high risk of developing Alzheimer's disease. In addition, the method of an embodiment of the present disclosure may be used clinically to determine treatment by diagnosing Alzheimer's disease at an early stage and selecting the most appropriate treatment method.

As used herein, the term "predicting an onset of Alzheimer's disease" means determining whether there is a possibility of developing Alzheimer's disease, whether there is a relatively high probability of developing Alzheimer's disease, or whether Alzheimer's disease has already occurred in a target subject. With respect to the aspects of an embodiment of the present disclosure, the term may refer to a case in which the possibility of developing Alzheimer's disease is present or high, or a case in which Alzheimer's disease has already been developed. As such, by predicting a risk of onset and selecting a person with a high risk of onset of Alzheimer's disease, it is possible to provide a treatment method that delays the time of onset through appropriate measures in the early stage.

The beta amyloid protein or *Staphylococcus aureus* strains are known proteins, and thus may be prepared using the antibody used in an embodiment of the present disclosure as an antigen according to a common method widely known in the immunology field. The beta amyloid protein used as an antigen of the antibody according to an embodiment of the present disclosure may be naturally extracted or synthesized, and may be prepared by a recombinant method based on a DNA sequence. According to the genetic recombination technique, a nucleic acid encoding the beta amyloid protein may be inserted into an appropriate expression vector, host cells may be cultured to express the beta amyloid protein in a transformant transformed with a recombinant expression vector, and then the beta amyloid protein may be recovered from the transformant.

For example, a polyclonal antibody may be produced by a method of injecting an antigen of the beta amyloid protein into an animal, collecting blood from the animal, and obtaining serum comprising an antibody. The antibody may be prepared using several warm-blooded animals such as a horse, a cow, a goat, sheep, a dog, a chicken, a turkey, a rabbit, a mouse, or a rat.

Also, a monoclonal antibody may be prepared using a known fusion method (Kohler and Milstein, European J. Immunol. 6:511-519, 1976), a recombinant DNA method (U.S. Pat. No. 4,816,567) and a phage antibody library technique (Clackson et al., Nature, 352, 624-628, 1991; Marks et al., J. Mol. Biol. 222, 58:1-597, 1991).

In an embodiment of the present disclosure, the method of detecting a protein is not particularly limited as long as the detection is based on a method for measuring the expression level of a protein known in the art, but as an example, it is possible to detect or measure the protein using an antibody that specifically binds to the protein. Specifically, the detection of the protein in an embodiment of the present disclosure is not limited to, but may be based on any one selected from the group consisting of, for example, Western blotting, an enzyme linked immunosorbent assay (ELISA), a radioimmunoassay, radioimmunodiffusion, Ouchterlony immunodiffusion, rocket immunoelectrophoresis, immunostaining (comprising immunohistochemical staining, immunocytochemical staining, immunofluorescence staining, and the like), an immunoprecipitation assay, a complement fixation assay, fluorescence activated cell sorter (FACS), surface plasmon resonance (SPR), or protein chips.

In an embodiment of the present disclosure, the subject sample may be a tonsil tissue. Tonsils are organs located in the back of the throat and nose, and are rich in lymphocytes, and are organs that perform immune functions in our bodies.

In an embodiment of the present disclosure, the tonsil may be a palatine tonsil, but is not limited thereto. The palatine tonsil is a tonsil in the roof of the mouth, a kind of lymph node, which is active mainly in children and is known to play a role in preventing infections such as the respiratory tract.

In an embodiment of the present disclosure, the term "tonsillectomy" refers to surgically removing the tonsils when daily life is inconvenient due to enlargement of the tonsils, particularly the palatine tonsils. In general, bilateral palatine tonsils are resected using an electrocautery, and adenoids in the nasopharynx are resected using an endoscopic microdebrider. Tonsillectomy may prevent degenerative brain diseases that may occur in the aging process, especially Alzheimer's disease, in advance, and tonsillectomy may be used in adults or the elderly in the sense of removing the reservoir of pathogens, but is not limited thereto.

In addition, an embodiment of the present disclosure provides a composition for predicting a risk of developing Alzheimer's disease, wherein the composition comprises one or more selected from the group consisting of: a substance for detecting an expression amount of beta amyloid protein or an accumulation amount thereof; and a substance for detecting an expression amount of *Staphylococcus aureus*, and wherein the composition uses tonsils as a sample.

In an embodiment of the present disclosure, the substance to be detected may be a probe, antibody, or aptamer specific to beta amyloid or *Staphylococcus aureus*, but is not limited thereto.

In addition, an embodiment of the present disclosure provides a use of a composition for predicting a risk of developing Alzheimer's disease, wherein the composition comprises one or more selected from the group consisting of: a substance for detecting an expression amount of beta amyloid protein or an accumulation amount thereof; and a substance for detecting an expression amount of *Staphylococcus aureus*, and wherein the composition uses tonsils as a sample.

In addition, an embodiment of the present disclosure provides a use of a composition for preparing an agent for predicting a risk of developing Alzheimer's disease, wherein the composition comprises one or more selected from the group consisting of: a substance for detecting an expression amount of beta amyloid protein or an accumulation amount thereof, and a substance for detecting an expression amount of *Staphylococcus aureus*, and wherein the composition uses tonsils as a sample.

In addition, an embodiment of the present disclosure provides a kit for predicting a risk of developing Alzheimer's disease, wherein the kit comprises the composition.

The kit of an embodiment of the present disclosure may further comprise a tool and/or a reagent known in the art used for immunological analysis in addition to a substance for detecting an expression amount or accumulation amount of the beta amyloid protein of an embodiment of the present disclosure, and a substance for detecting an expression amount of *Staphylococcus aureus*.

The immunological analysis may be carried out with any of the methods capable of measuring the binding of an antibody to an antigen. Such methods are known in the art comprise, for example, immunocytochemistry and immunohistochemistry, radioimmunoprecipitation, an ELISA, immunoblotting, a Farr assay, immunoprecipitation, latex agglutination, hemagglutination, nephelometry, immunodiffusion, counter-current electrophoresis, single radical immunodiffusion, a protein chip assay, and an immunofluorescence assay.

As a tool and/or reagent used in immunological analysis, a suitable carrier or support, a marker capable of producing a detectable signal, a solubilizer, or a cleaning agent may be comprised. When a marker substance is an enzyme, a substrate capable of measuring enzyme activity and a reaction stopping agent may be comprised.

The antigen comprised in the kit of an embodiment of the present disclosure is preferably fixed to a suitable carrier or support using various methods disclosed in a document (Antibodies: A Laboratory Manual, Harlow & Lane; Cold SpringHarbor, 1988), and examples of suitable carriers and supports comprise agarose, cellulose, nitrocellulose, dextran, Sephadex, Sepharose, a liposome, carboxymethyl cellulose, polyacrylamide, polystyrene, gabbro, filter paper, an ion exchange resin, a plastic film, a plastic tube, glass, a polyamine-methyl vinyl-ether-maleic acid copolymer, an amino acid copolymer, an ethylene-maleic acid copolymer, nylon, cup, and flat packs. As other solid substrates, there are a cell culture plate, an ELISA plate, a tube, and a polymeric membrane. The support may have a random form, for example, globular (beads), cylindrical (test tube or inside of well), and plane (sheet, test strip) forms.

The marker capable of producing a detectable signal is able to qualitatively or quantitatively measure the formation of an antigen-antibody complex, and may be, for example, an enzyme, a fluorescent material, a ligand, a luminous material, a microparticle, a redox molecule or a radioisotope. As an enzyme, β-glucuronidase, β-D-glucosidase, a urease, a peroxidase, alkaline phosphatase, acetylcholinesterase, glucose oxidase, a hexokinase, malate dehydrogenase, glucose-6-phosphate dehydrogenase, or invertase may be used. As a fluorescent material, fluorescein, isothiocyanate, rhodamine, phycoerythrin, phycocyanin, allophycocyanin, or fluorescein isothiocyanate may be used. As a ligand, a biotin derivative may be used, and as a luminous material, acridinium ester, a luciferin, or luciferase may be used. As a microparticle, colloidal gold or colored latex may be used, and as a redox molecule, ferrocene, a ruthenium complex, a viologen, a quinone, a Ti ion, a Cs ion, diimide, 1,4-benzoquinone or hydroquinone may be used. However, other than the substances listed above, any one capable of being used in immunological analysis may be used.

As used herein, the terms "about or approximately" or "substantially" or the like are intended to have meanings close to numerical values when unique allowable manufacturing and substance errors are presented to the mentioned meaning, and intended to prevent accurate or absolute numerical values disclosed for understanding of the present disclosure from being illegally or unfairly used by any unconscionable third party.

MODE FOR DISCLOSURE

Hereinafter, a preferred embodiment is presented to aid understanding of the present disclosure. However, the following examples are provided to more easily understand the present disclosure, and the content of the present disclosure is not limited by the following examples.

Example 1. Identification of Expression of Beta Amyloid in Human Palatine Tonsil Tissue After collecting human palatine tonsil tissue through tonsillectomy, paraffin-embedded samples were prepared and beta amyloid peptide-specific monoclonal antibody 6E10 (beta amyloid antibody (6E10, 1:100; BioLegend, 803002)) was used. Through immunofluorescence staining, it was evaluated whether expression of beta amyloid, a major causative protein of Alzheimer's disease, was identified in human tonsil tissue.

The tissue samples were observed for the expression level of beta amyloid through H&E staining and immunofluorescence staining using beta amyloid antibody. Specifically, tissue fixed in 4% paraformaldehyde was embedded in paraffin to make blocks, sectioned to a thickness of 4-5 μm, and subjected to deparaffinization, and then H&E staining and immunofluorescence staining. To examine the expression of beta amyloid, paraffin sections that had undergone the deparaffinization process were treated with 97% formic acid for 3 minutes, washed three times with PBS, and treated with 1% normal goat serum for 1 hour at room temperature to block non-specific binding. Then, a beta amyloid antibody (6E10, 1:100; BioLegend, 803002) was treated at room temperature for 1 hour and washed with PBS, and the primary antibody was treated with a fluorescent secondary antibody (Alexa Fluor 594-conjugate or 488-conjugate) and reacted at room temperature for 1 hour. The reactant was washed with PBS and mounted with a mounting solution, and then the expression level of beta amyloid was analyzed by immunofluorescence staining using confocal microscopy. DAPI means 4',6-diamidino-2-phenylindole for counting staining.

TABLE 1

Patient characteristics of FIG. 1

| | Age | Gender | Tonsillar disease |
|---|---|---|---|
| #1 | 7 | Female | Tonsillitis |
| #2 | 49 | Female | Tonsillitis |
| #3 | 52 | Female | Tonsillitis |
| #4 | 53 | Female | Tonsillitis |

As shown in FIG. 1, it was identified that beta amyloid was deposited around the tonsils and lymph nodes in palatal tonsil tissues of different ages. In addition, it was identified through H&E staining of the tissue that it exhibited a multi-layered stratified surface epithelium.

Example 2. Identification of Expression of Beta Amyloid and *Staphylococcus aureus* in Human Palatine Tonsil Tissue After collecting human palatine tonsil tissue through tonsillectomy, paraffin-embedded samples were prepared and beta amyloid peptide-specific monoclonal antibody 6E10 and *Staphylococcus aureus* strains specific antibody (anti-*Staphylococcus aureus*, Abcam) were used. Through immunofluorescence staining, it was evaluated how beta amyloid deposition and bacterial expression appeared in human tonsil tissue.

TABLE 2

Figure 2:
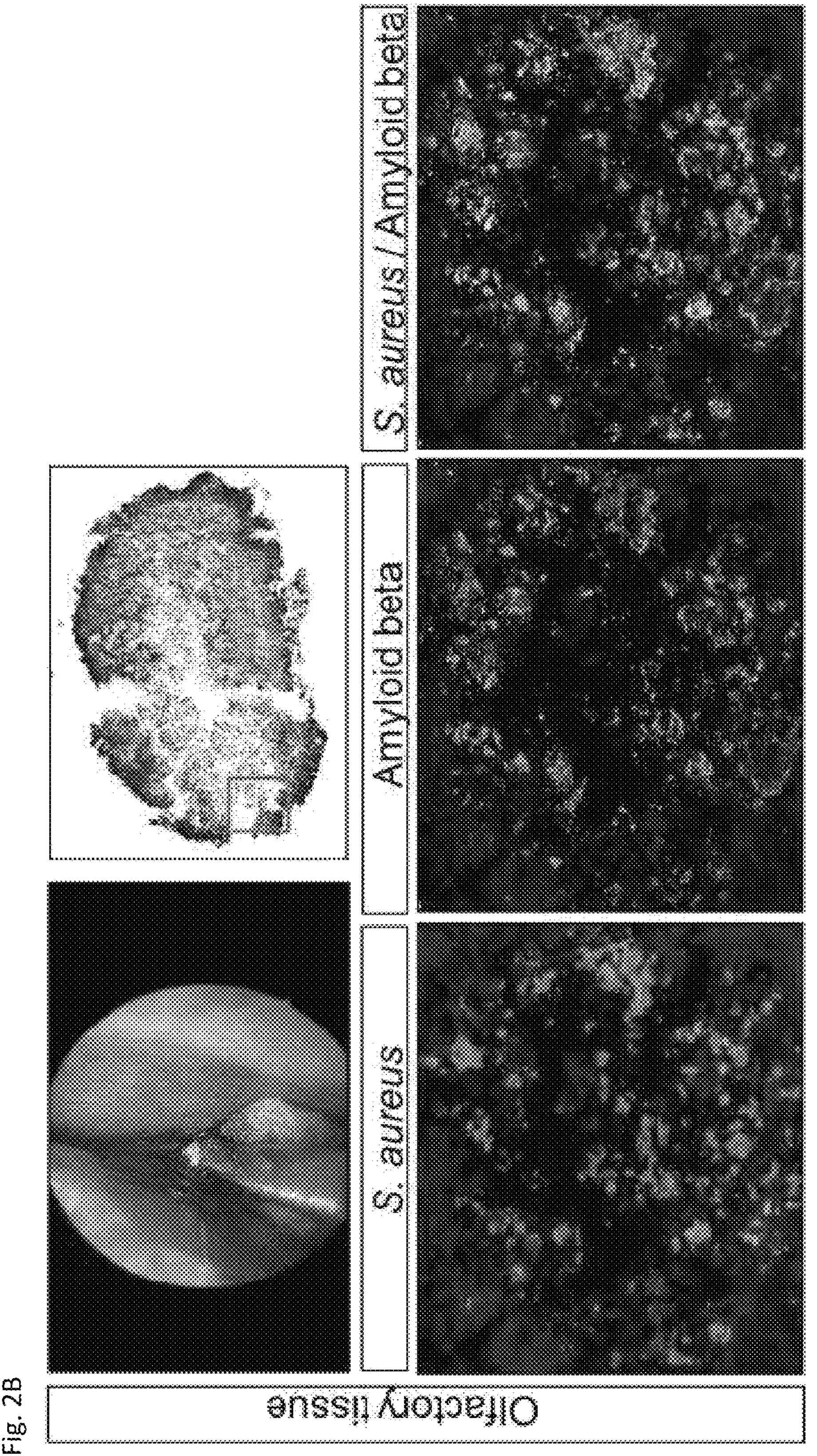
FIGS. 2A and 2B are diagrams showing the expression level of beta amyloid and *Staphylococcus aureus* (*S. aureus*) using immunofluorescence staining in seven different tonsil tissues obtained through tonsillectomy and olfactory surrounding tissue obtained through neurosurgery.

Patient characteristics of FIG. 2A

| | Age | Gender | Tonsillar disease |
|---|---|---|---|
| #1 | 9 | Female | Tonsillitis |
| #2 | 11 | Male | Tonsillitis |
| #3 | 16 | Female | Tonsillitis |
| #4 | 43 | Female | Tonsillitis |

TABLE 2-continued

| Patient characteristics of FIG. 2A | | | |
|---|---|---|---|
| | Age | Gender | Tonsillar disease |
| #5 | 7 | Female | Tonsillitis |
| #6 | 8 | Female | Tonsillitis |
| #7 | 8 | Male | Tonsillitis |

As shown in FIG. 2A, beta amyloid protein expression and *Staphylococcus aureus* strain expression were identified in seven palatine tonsil tissues of different ages and genders. In some of these tissues, it was identified that *Staphylococcus aureus* strains were present around or inside beta amyloid plaques.

Moreover, as shown in FIG. 2B, as a result of immunofluorescence staining using tissue collected from the olfactory mucosal epithelium tissue of an older brain tumor patient, it was identified that the expression of beta amyloid protein and expression of *Staphylococcus aureus* strains were high, and that the expression of the bacteria was observed in the part where the beta amyloid protein was deposited.

Example 3. Identification of Expression of Beta Amyloid Protein Fragments in Human Palatine Tonsil Tissue After collecting human palatine tonsil tissue through tonsillectomy, a protein was extracted from the tissue using RIPA lysis buffer, and the expression pattern of beta amyloid protein fragments in palatine tonsil tissue was identified using a Western blotting method.

Tissues obtained by tonsillectomy were ground using RIPA buffer (Thermo Fisher Scientific) to extract proteins, and then expression of a soluble beta amyloid protein in the tissues was identified by a Western blotting method. Electrophoresis was performed using NuPAGE 4-12% (w/v) and 12% (w/v) Bis-Tris Protein Gels (Thermo Fisher Scientific), followed by transfer to a nitrocellulose membrane having a pore size of 1 μm. To block non-specific binding, the membrane was blocked with 5% (w/v) milk and incubated at 4° C. for 24 hours using a beta amyloid antibody (6E10, 1:100; BioLegend, 803002). After washing the membrane three times with TBS solution (TBST) comprising Tween 20, protein expression was identified by reacting the same at room temperature for 1 hour using the secondary antibody with HRP attached to the primary antibody, washing the same three times with TBST solution, and then using ECL (enhanced chemiluminescence) detection reagents (Thermo Fisher Scientific).

Figures 3, 3A:
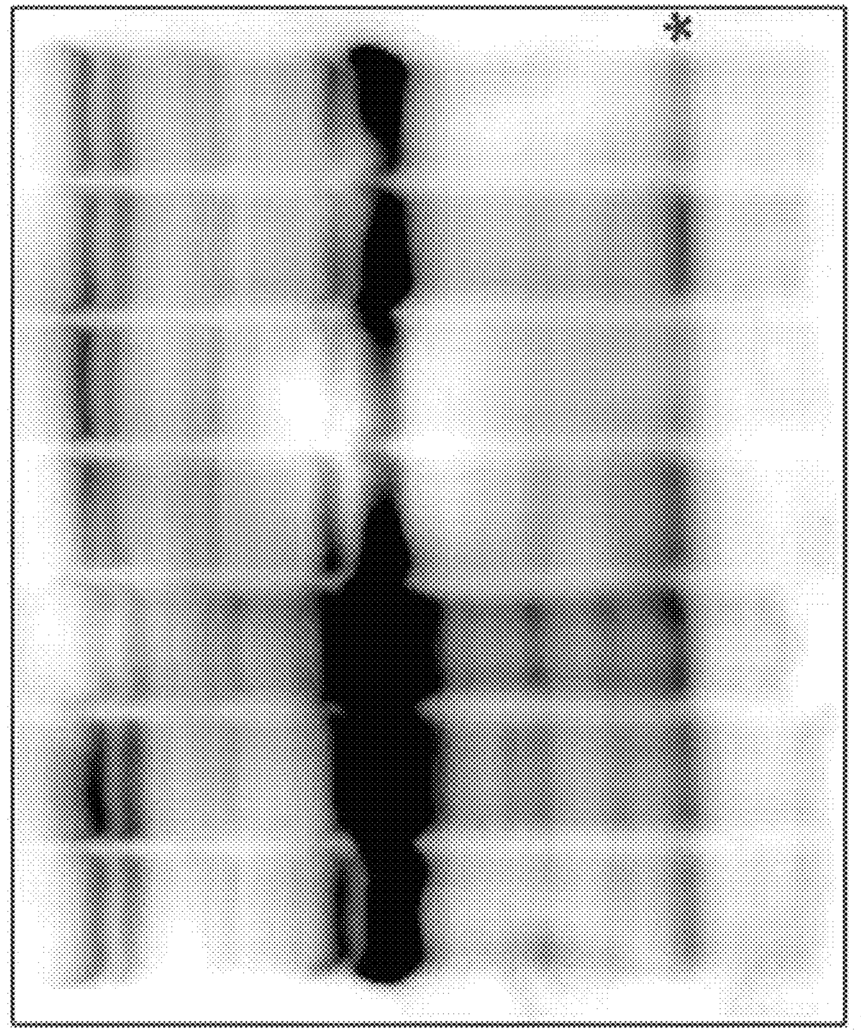
FIGS. 3A and 3B are diagrams identifying the expression of beta amyloid fragments by Western blotting after protein extraction from seven different tonsil tissues obtained through tonsillectomy.
Figures 3, 3B:
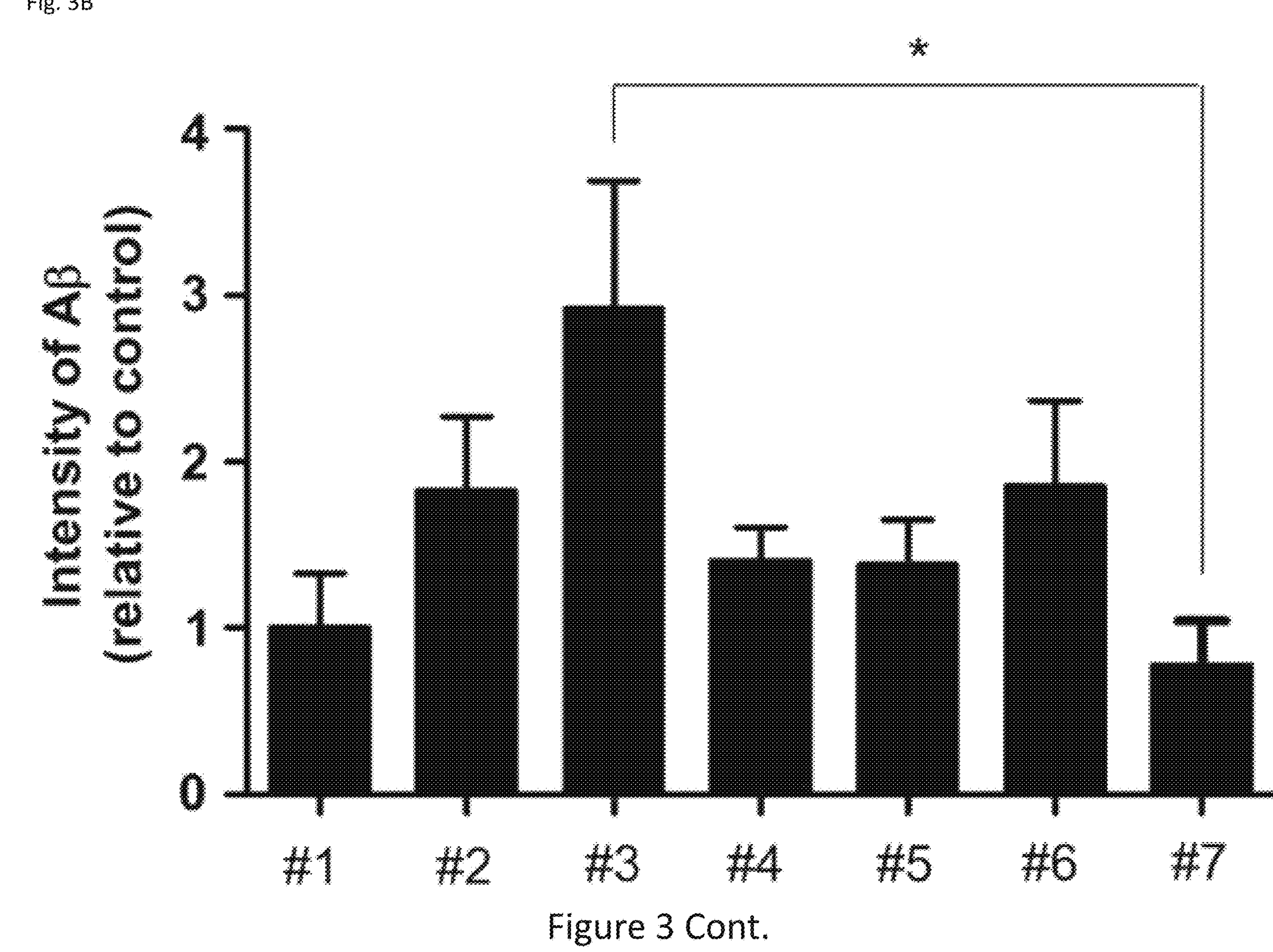
Figures 4, 4A:
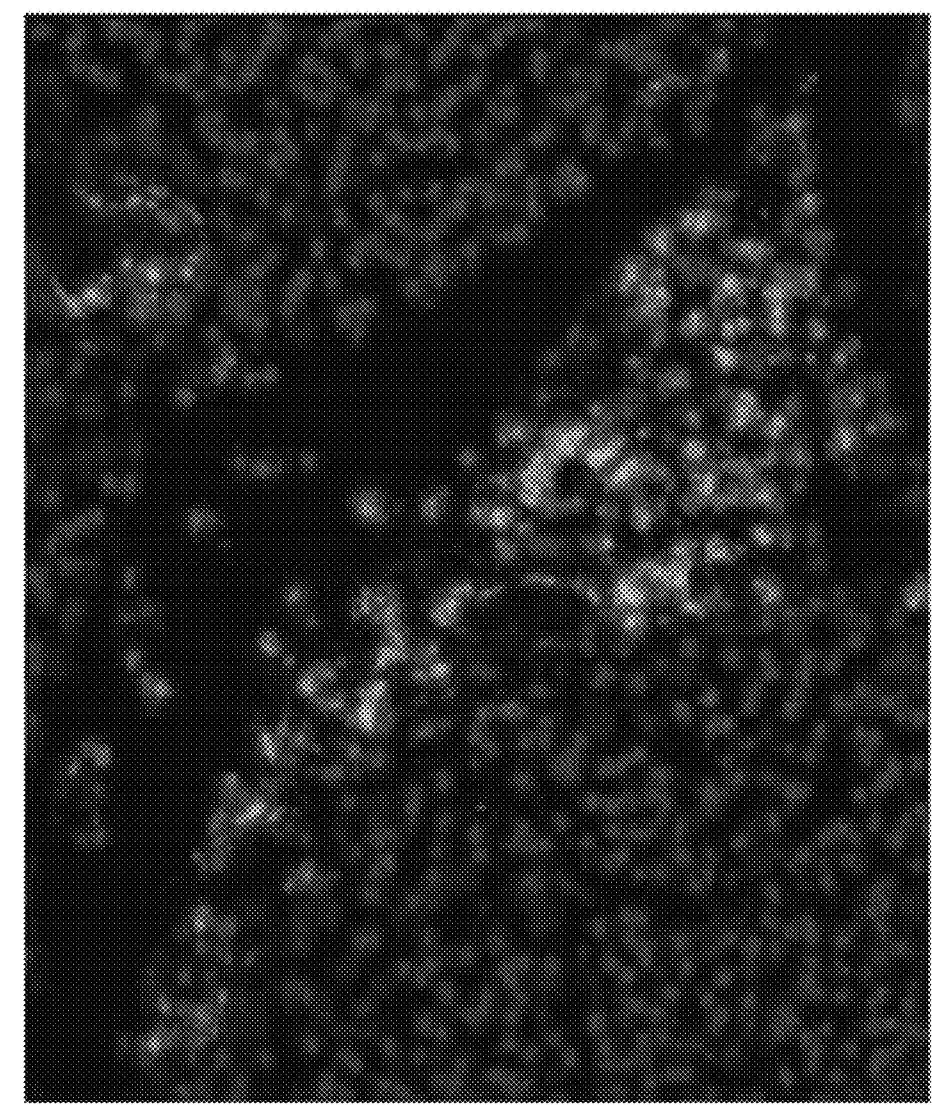
Figures 4, 4B:
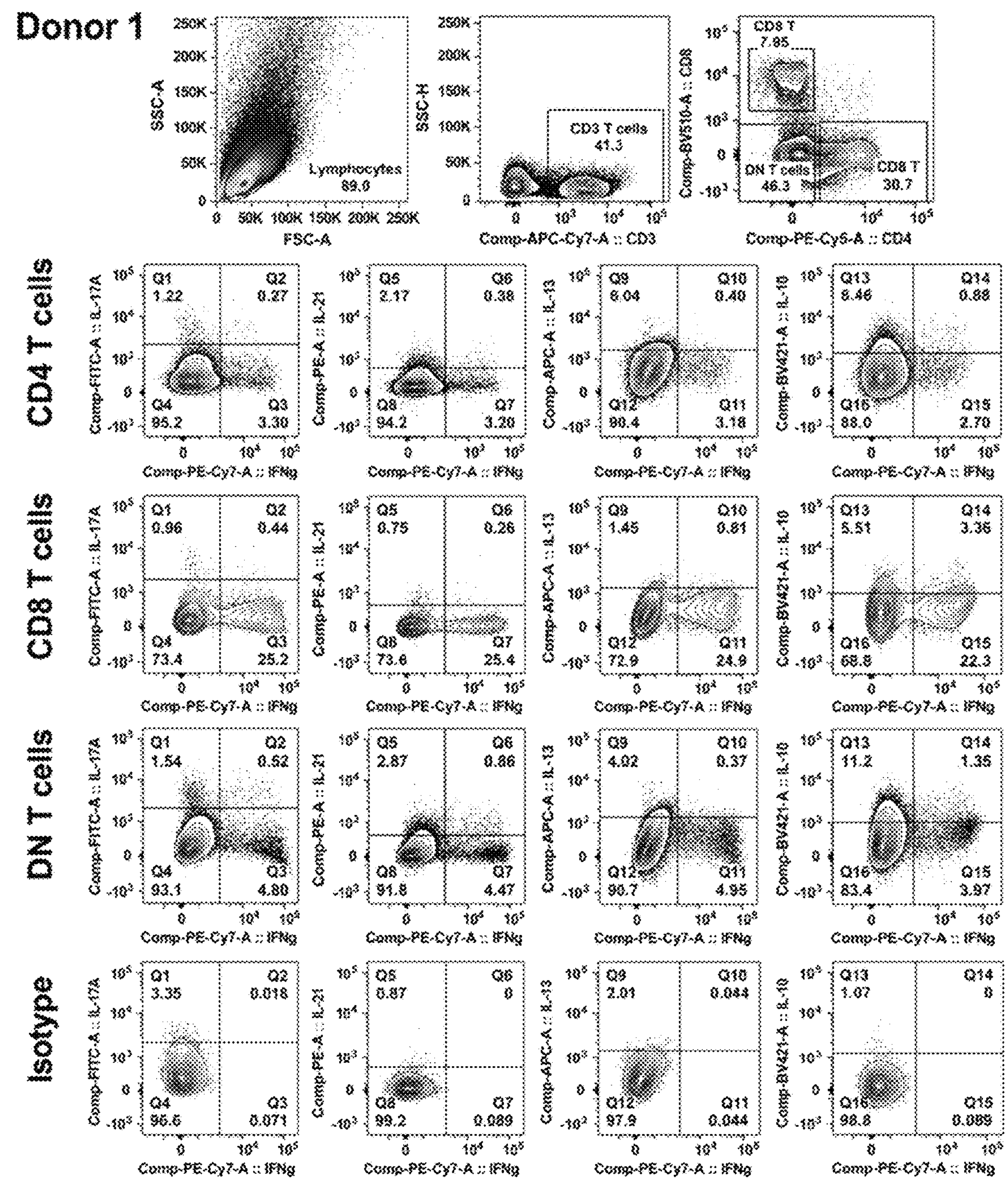
Figures 4, 4C:
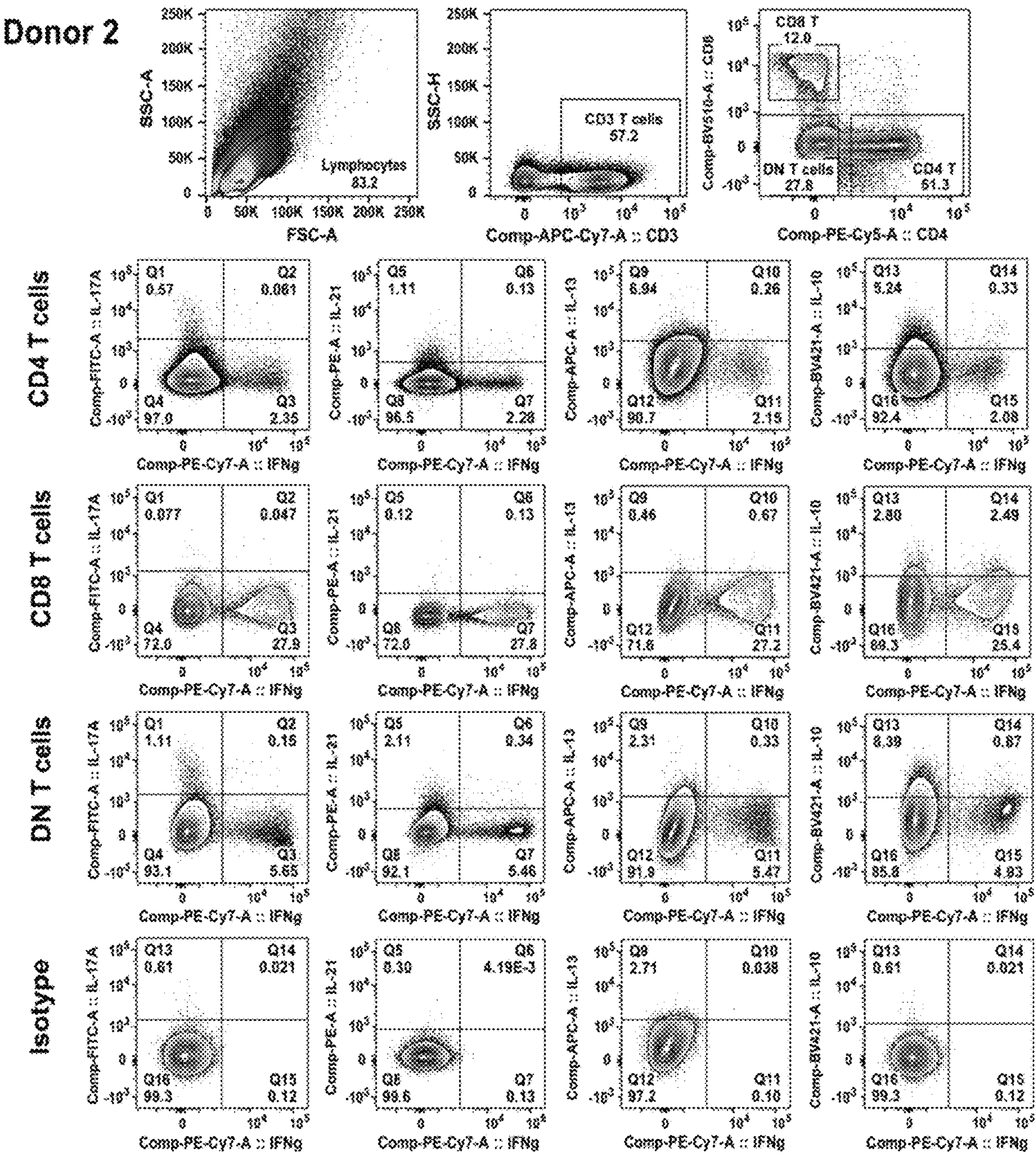
Figures 4, 4D:
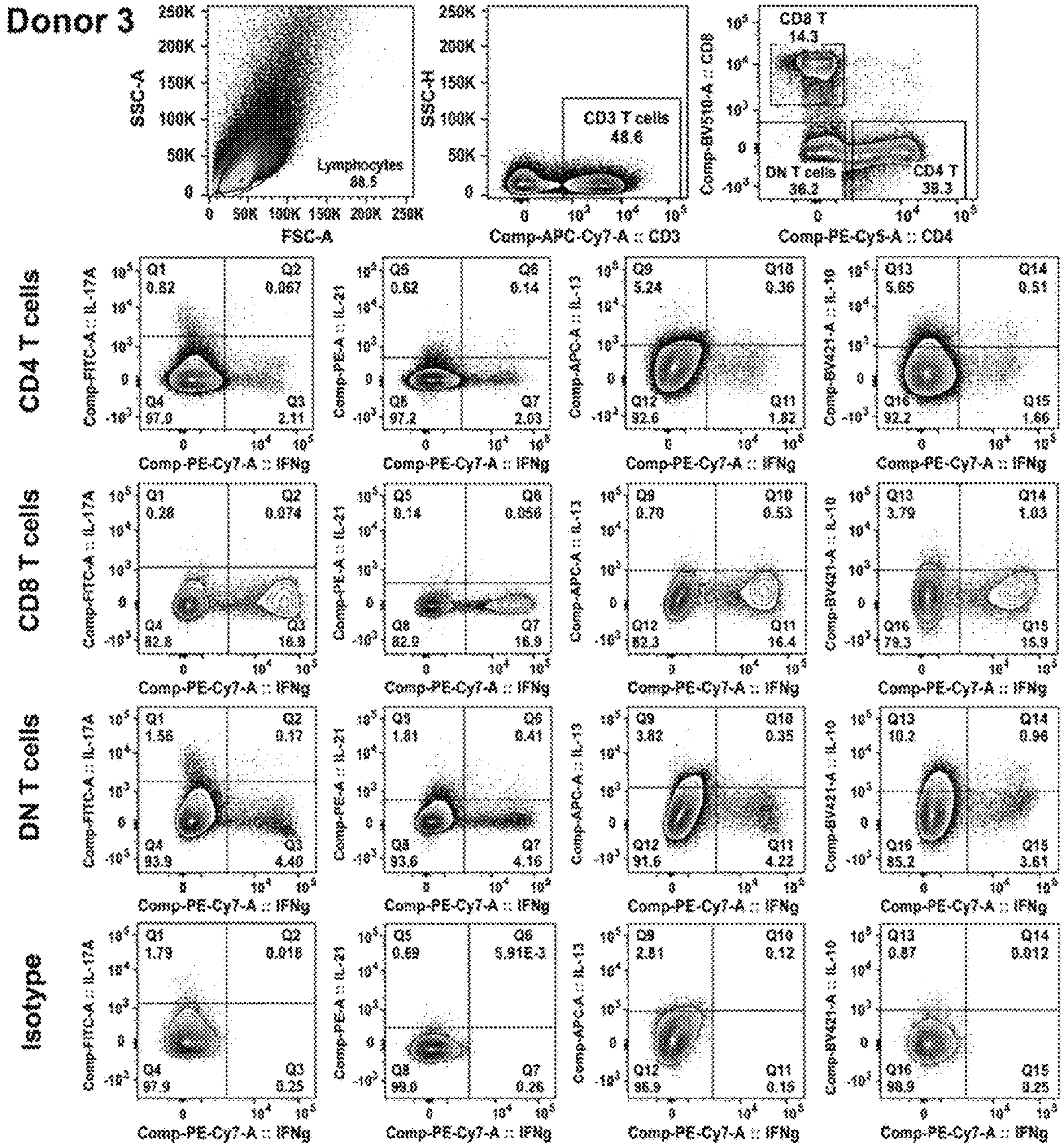
Figures 4, 4E:
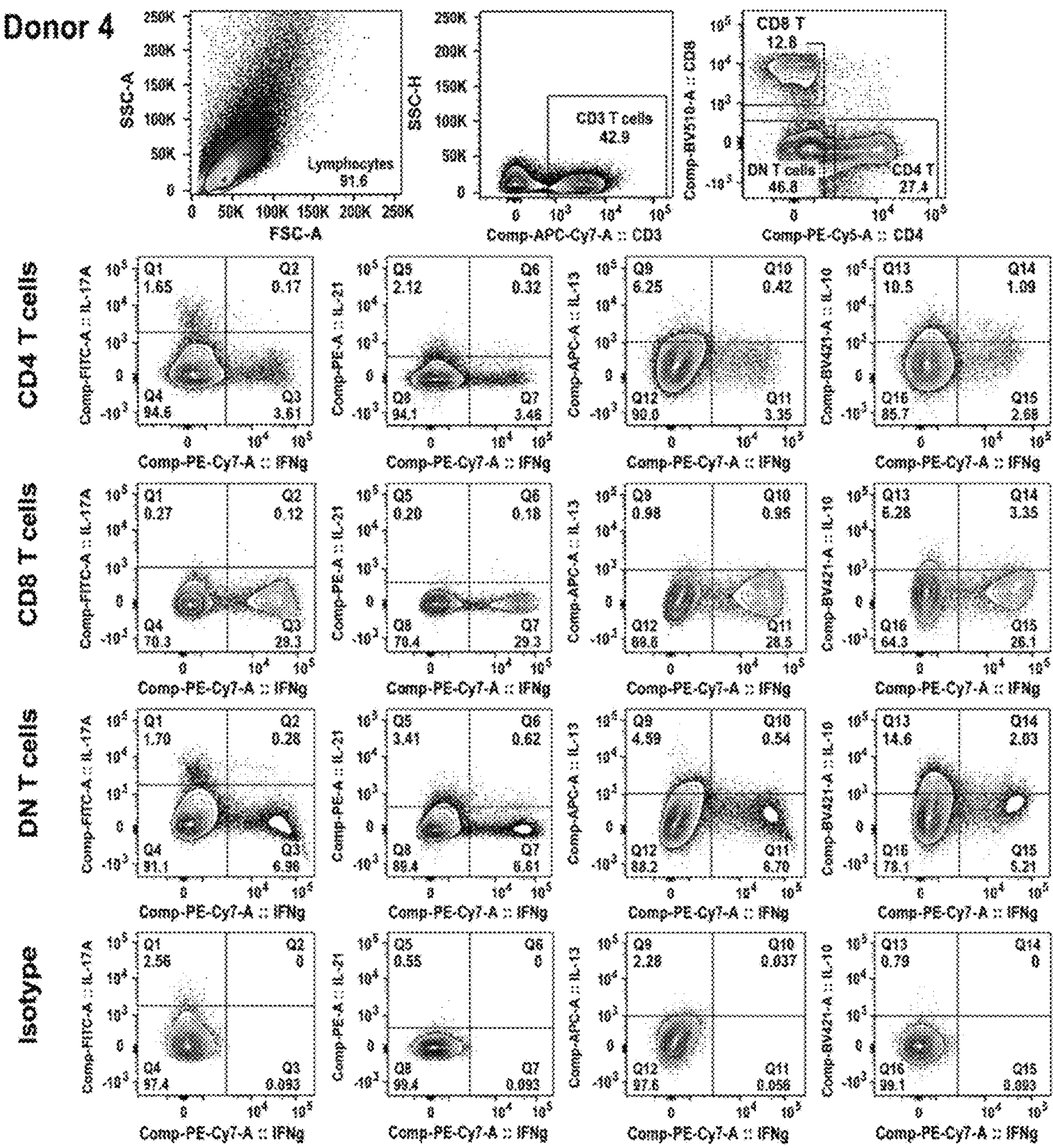
Figures 4, 4F:
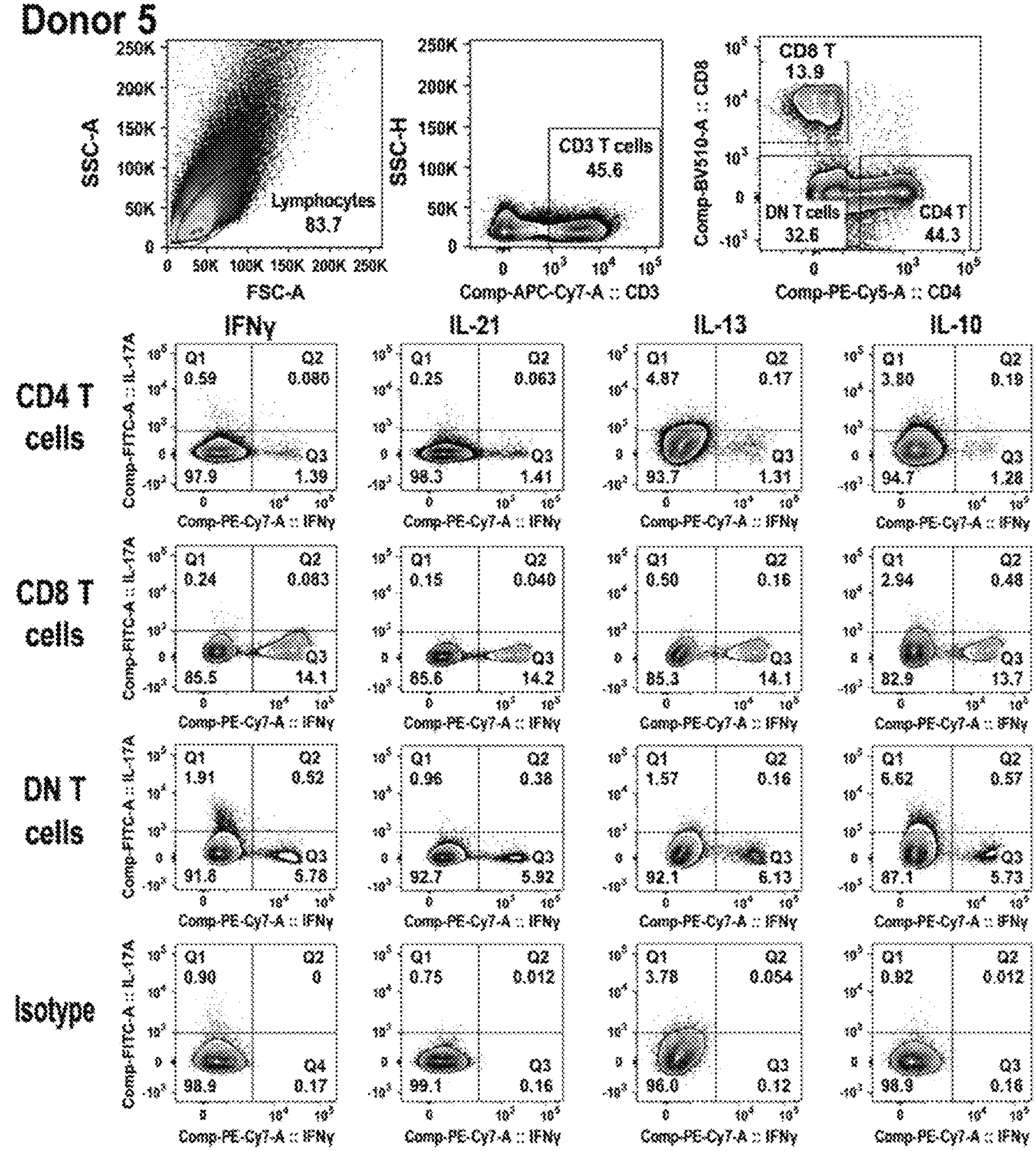
Figures 4, 4G:
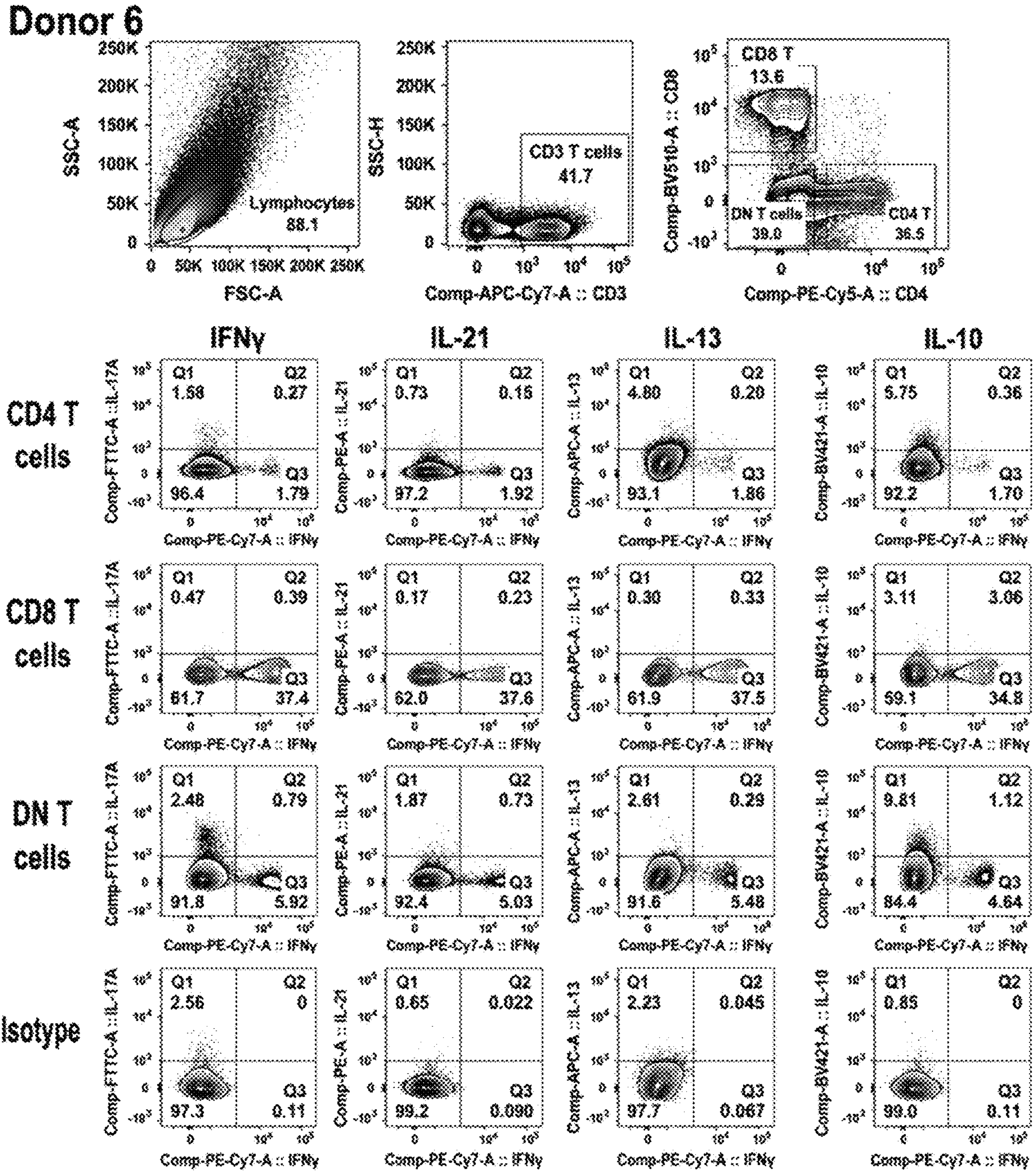
Figures 4, 4H:
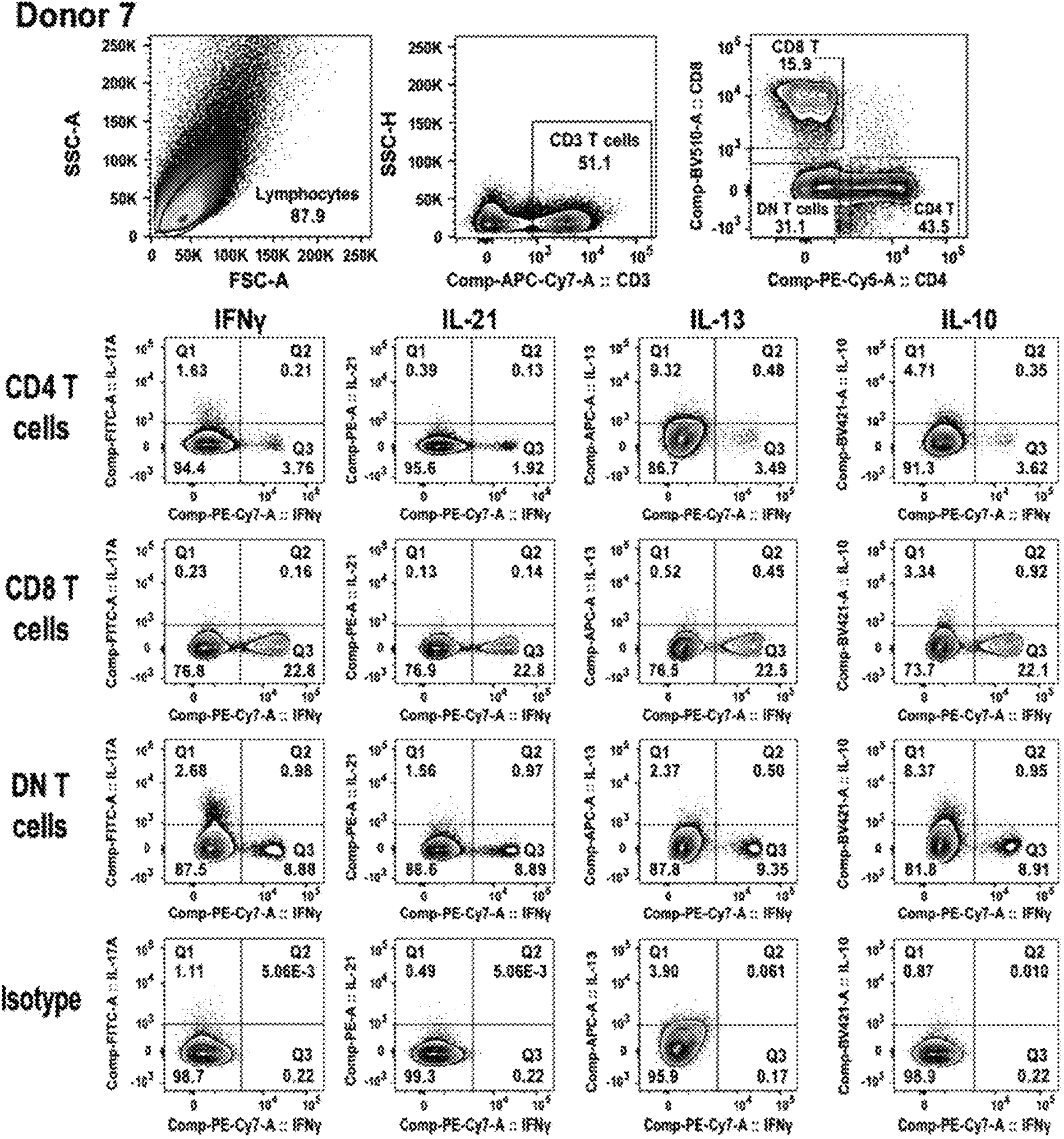

As a result, as shown in FIGS. 3A and 3B, it was identified that beta amyloid protein fragments of various sizes were present in tonsil tissues of different ages and genders. Among them, it was identified that the expression of an oligomer (about 15 kDa in size) important for beta amyloid toxicity was different for each subject.

Example 4. Identification of Beta Amyloid Protein and *Staphylococcus Aureus* (*S. aureus*) Expression and T Cell Relationship in Human Palatine Tonsil Tissue After collecting human palatine tonsil tissue through tonsillectomy, intracellular T cell cytokine expression was analyzed in seven different palatine tonsil tissues. Specifically, after isolating mononuclear cells from each tissue, they were stained with fluorescent conjugated monoclonal antibodies such as CD4, IFN-γ, and IL17A, and IFN-γ and IL17A produced by T cells were analyzed using FACS.

Seven pieces of tissue obtained from tonsillectomy were finely cut and placed in RPMI-1640 medium comprising 10% FBS. Cells were obtained using a cell strainer, and only tonsillar mononuclear cells (TMC) were isolated by density gradient centrifugation using Ficoll-Hypaque™.

TMC was washed three times with sterile PBS and placed in RPMI-1640 medium comprising 10% FBS. Cells were stimulated for 4 hours with phorbol-12-myristate-13-acetate (PMA, 50 ng/ml) supplemented with ionomycin (500 ng/ml) in the presence of GolgiPlug (BD Bioscience). After staining the cells with fluorochrome-labeled CD3 (Biolegend), CD4 (Biolegend), and CD8 (Biolegend) antibodies at 4° C. for 30 minutes, the cells were fixed and permeabilized, and strained with the fluorochrome-labeled antibody. IFN-γ and IL-17A were re-suspended in FACS buffer for 1 hour at 4° C., and obtained through FACS Cantoll (BD Biosciences) using DIVA software. All pieces of data were analyzed using FlowJo software (FlowJo, LLC, Franklin Lakes, NJ).

As shown in FIGS. 4A to 4J, it was identified that the higher the activity of the T cells, the higher the expression of beta amyloid or the higher the bacteria. Accordingly, it was identified that the degree of T cell activity and the expression of beta amyloid protein or the expression of *Staphylococcus aureus* strains were related.

Example 5. Identification of Relationship Between Beta Amyloid Protein and *Staphylococcus Aureus* (*S. aureus*) Expression in Human Tonsil Tissue-Based Organoids After collecting human palatine tonsil tissue through tonsillectomy, a small isolated tissue was embedded in Matrigel and placed in a cell culture dish, and various growth factors were added to advanced DMEM/F12 medium and cultured in an incubator at 37° C. and 5% $CO_2$ environment. Tonsillar organoid culture medium prepared using human palatine tonsil tissue was treated with *Staphylococcus aureus* strains isolated from patients, cultured for at least 5 days, and then analyzed by H&E staining and immunofluorescence staining. The H&E staining and immunofluorescence staining methods were the same as those of the aforementioned examples.

Figures 5, 5A:
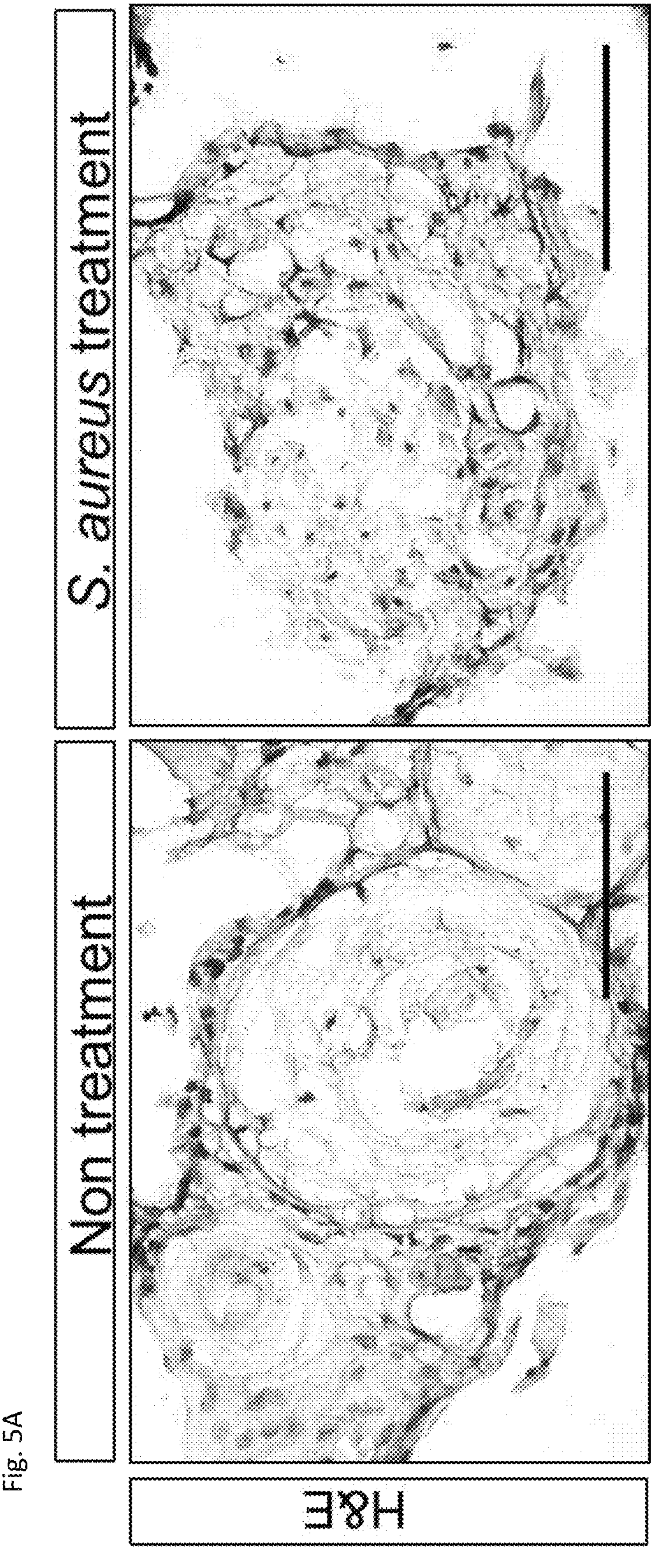
FIGS. 5A to 5D are diagrams identifying the effect of *Staphylococcus aureus* (*S. aureus*) on beta amyloid expression through H&E staining and immunofluorescence staining in tonsillar organoids prepared based on tonsil tissue obtained through tonsillectomy. The scale bar in FIG. 5*a* represents 100 μm.
Figure 5:
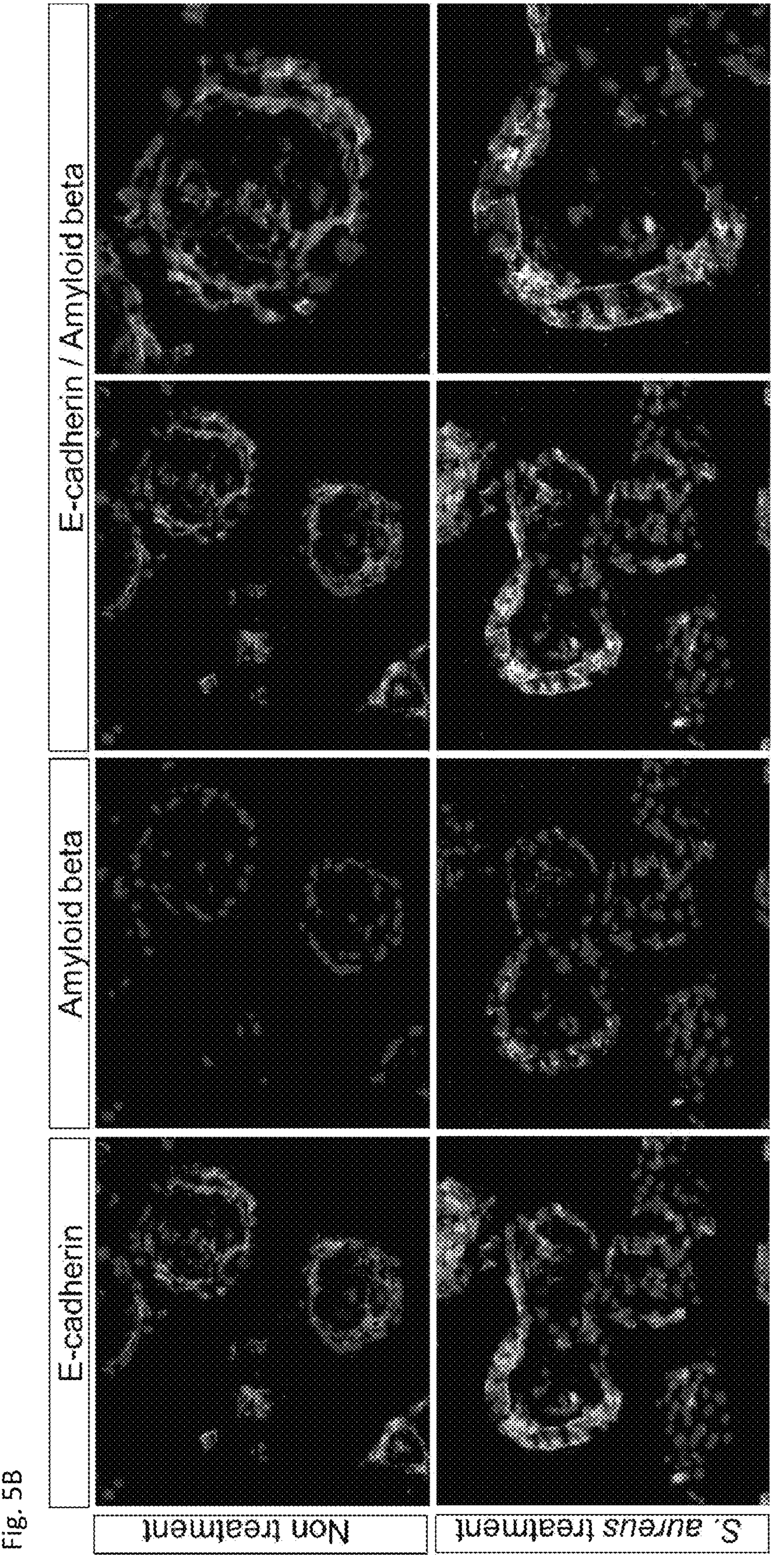

As shown in FIG. 5A, when the morphology of human tonsillar organoids was observed by H&E staining after treatment with *Staphylococcus aureus* strains, unlike tonsillar organoids cultured without bacterial treatment, histological damage to tonsillar organoids was observed in the case of bacterial treatment.

Figures 5, 5C:
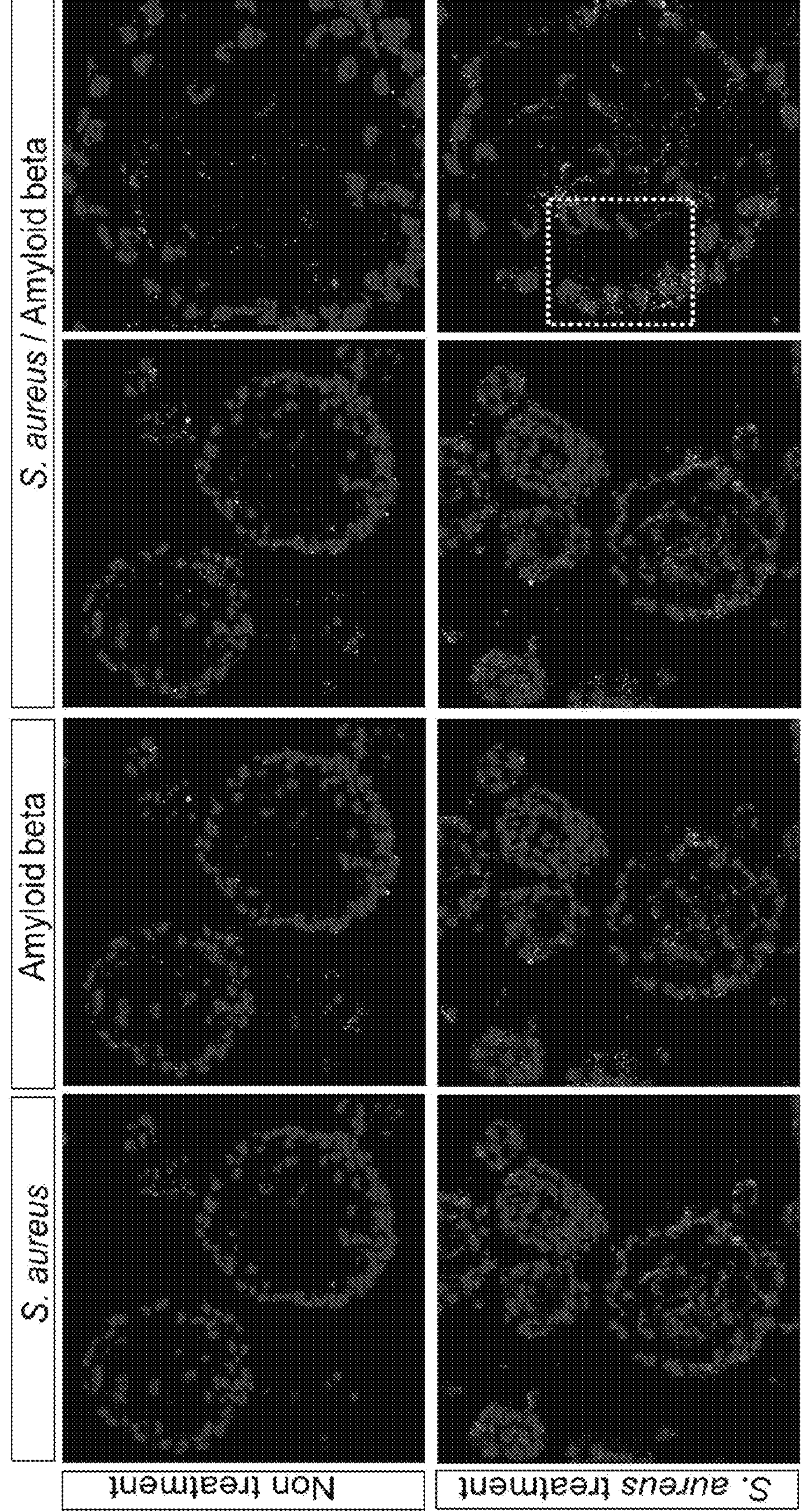
Figures 5, 5D:
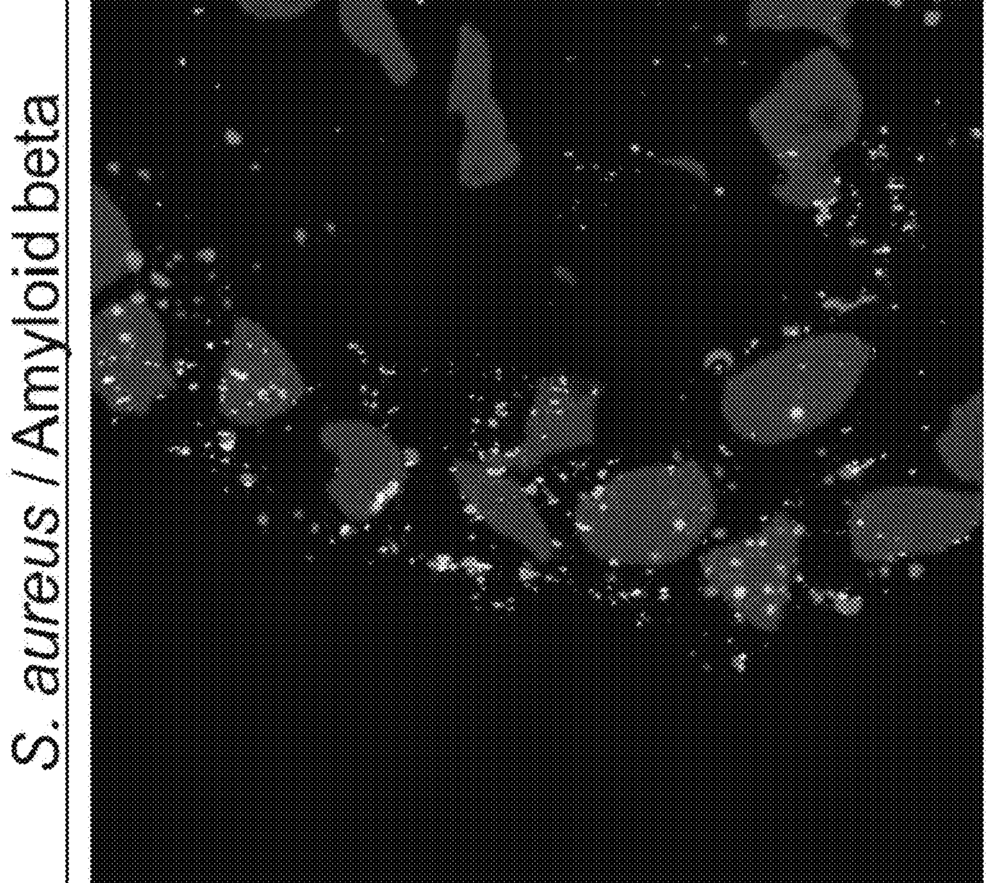

As shown in FIGS. 5B to 5D, compared to normal tonsillar organoids, the expression of beta amyloid protein increased in organoids treated with bacteria. In addition, it was observed that beta amyloid protein and bacteria co-expressed.

Example 6. Identification of Relationship Between Beta Amyloid Protein and *Staphylococcus Aureus* (*S. aureus*) Expression in Human Induced Pluripotent Stem Cell (Dedifferentiated Stem Cells, iPSC)-Based Brain Organoids To identify whether *Staphylococcus aureus* strains, which are present in the palatine tonsils, infect the actual brain through the periolfactory pathway (the space around the olfactory nerve that goes to the cribriformplate) or the peritrigeminal pathway (the passage around the sensory nerve branches), resulting in Alzheimer's disease, brain organoids were prepared from dedifferentiated stem cells and treated with *Staphylococcus aureus* strains.

First, $9\times10^3$ or $1\times10^4$ dedifferentiated stem cells induced from human blood were mixed with mTeSR™ medium, and then seeded into a U-bottom 96-well plate, respectively. The seeded cells were induced into spheroids for about 7 days in an incubator at 37° C. and 5% $CO_2$. Thereafter, for the formed spheroids, differentiation was induced for about 5-7 days using a differentiation medium comprising N2 supplement and MEM NEAA (Non-Essential Amino Acids). The medium was changed every 3 to 4 days until fully matured organoids were formed. In addition, a shaker was put into the incubator and cultured at a speed of 70 rpm at 37° C. and 5% $CO_2$ for about 30 to 40 days (see Korean Patent No. 10-2285600). *Staphylococcus aureus* strains isolated from a patient were treated with a brain organoid culture medium prepared using human dedifferentiated stem cells at a MOI concentration of 10 for 2 to 3 hours, and analyzed by H&E staining and immunofluorescence staining. H&E staining and immunofluorescence staining methods were the same as those of the aforementioned examples. Antibodies used were as follows: anti-Nestin (1:500, Santa Cruz Biotechnology Inc., SC-23927), anti-β-III tubulin (1:500, BioLegend, 801201), and anti-Iba-1 (1:500; Wako, Osaka, Japan).

Figures 6, 6A:
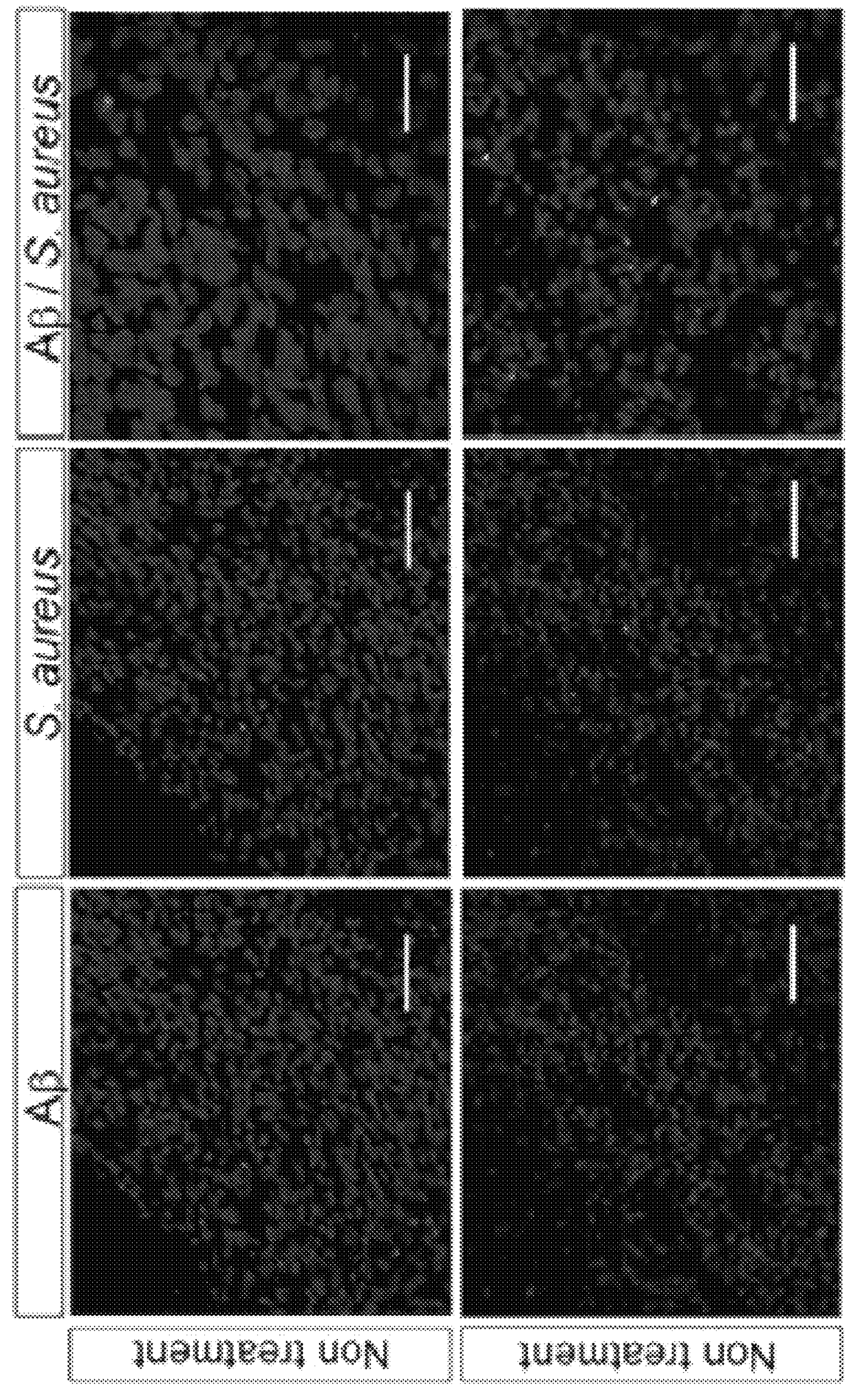
FIGS. 6A to 6F show the results of performing H&E staining and immunofluorescence staining on human dedifferentiated stem cell-based brain organoids.
Figures 6, 6B:
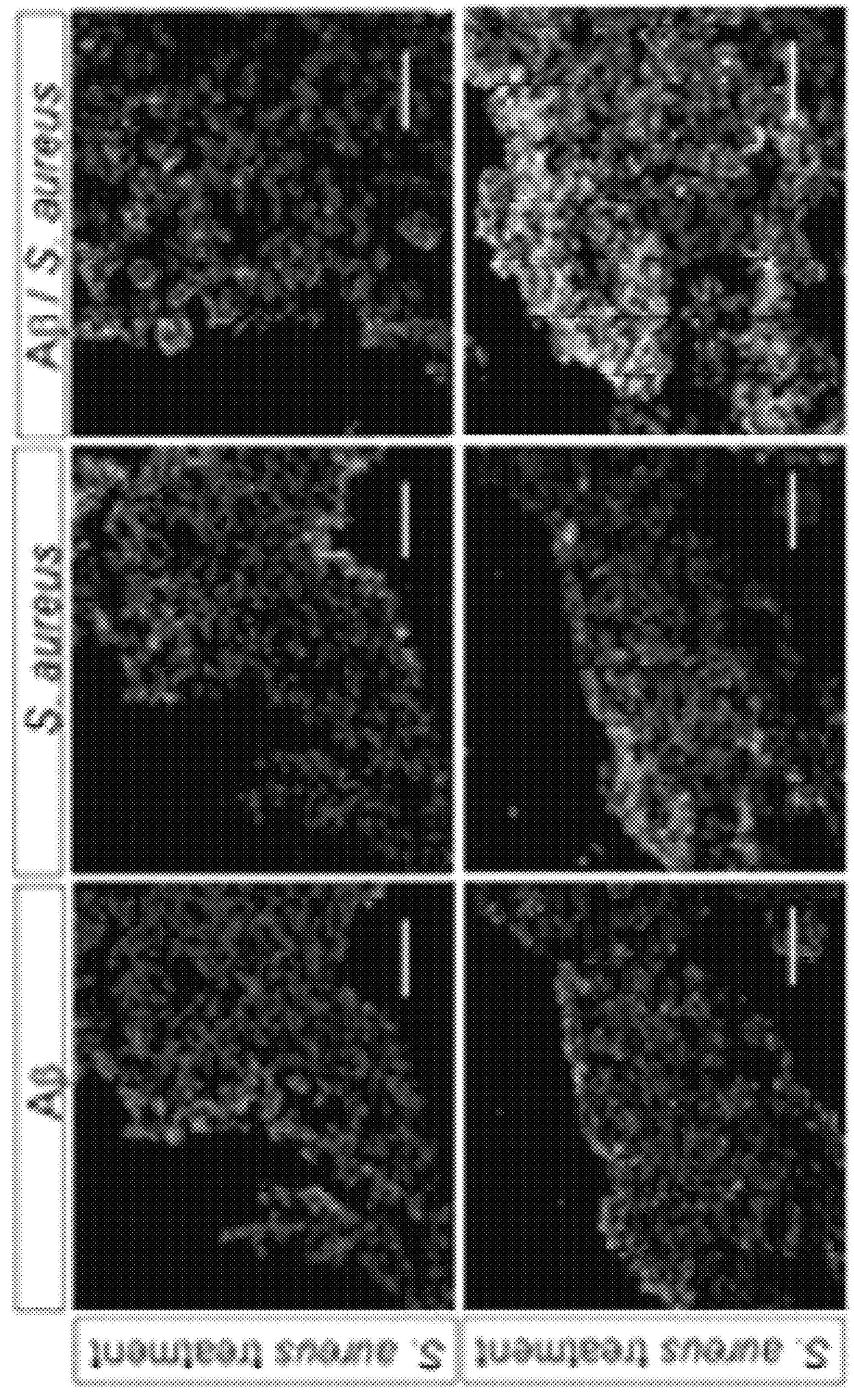
Figures 6, 6C:
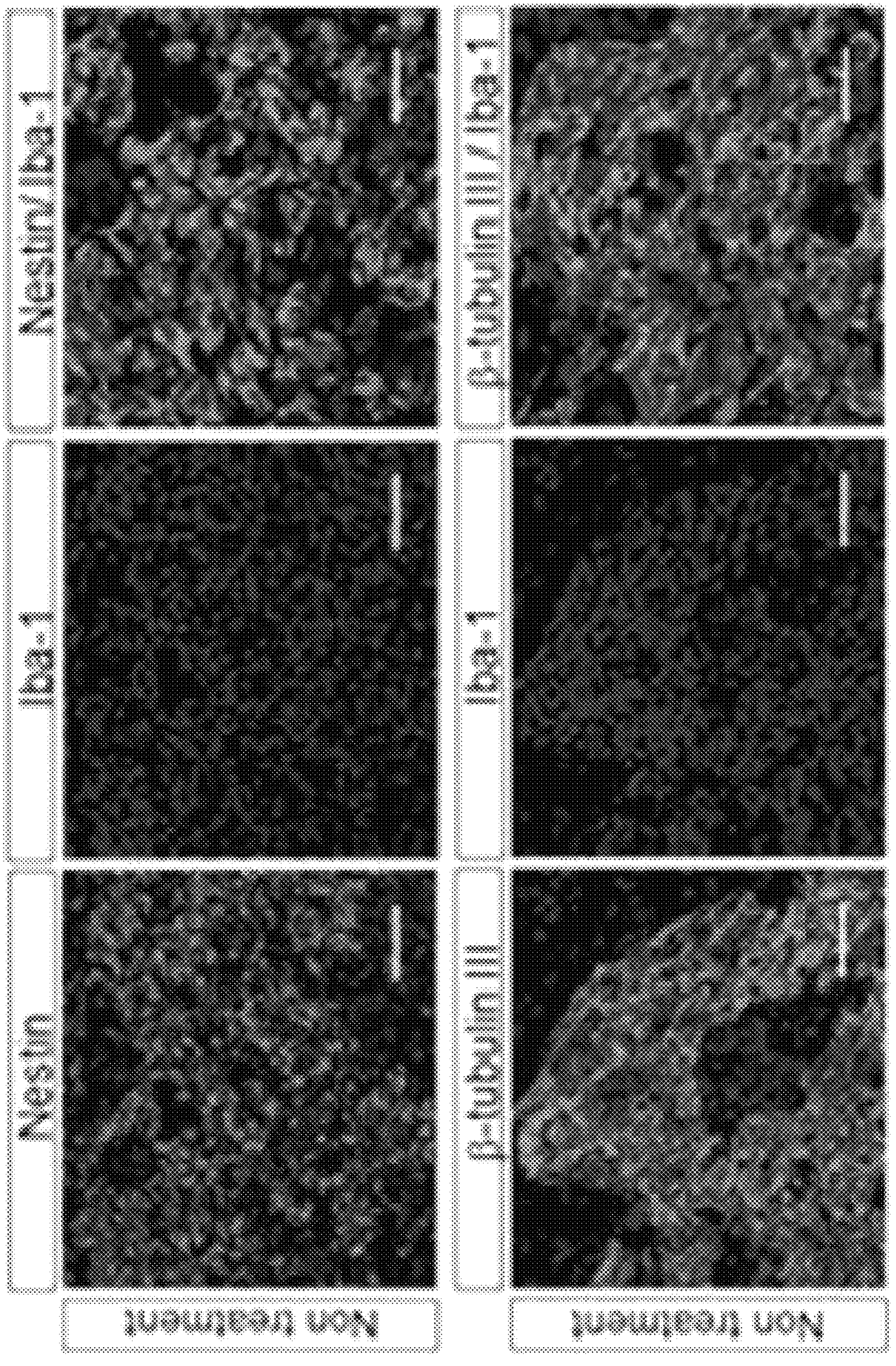
Figures 6, 6D:
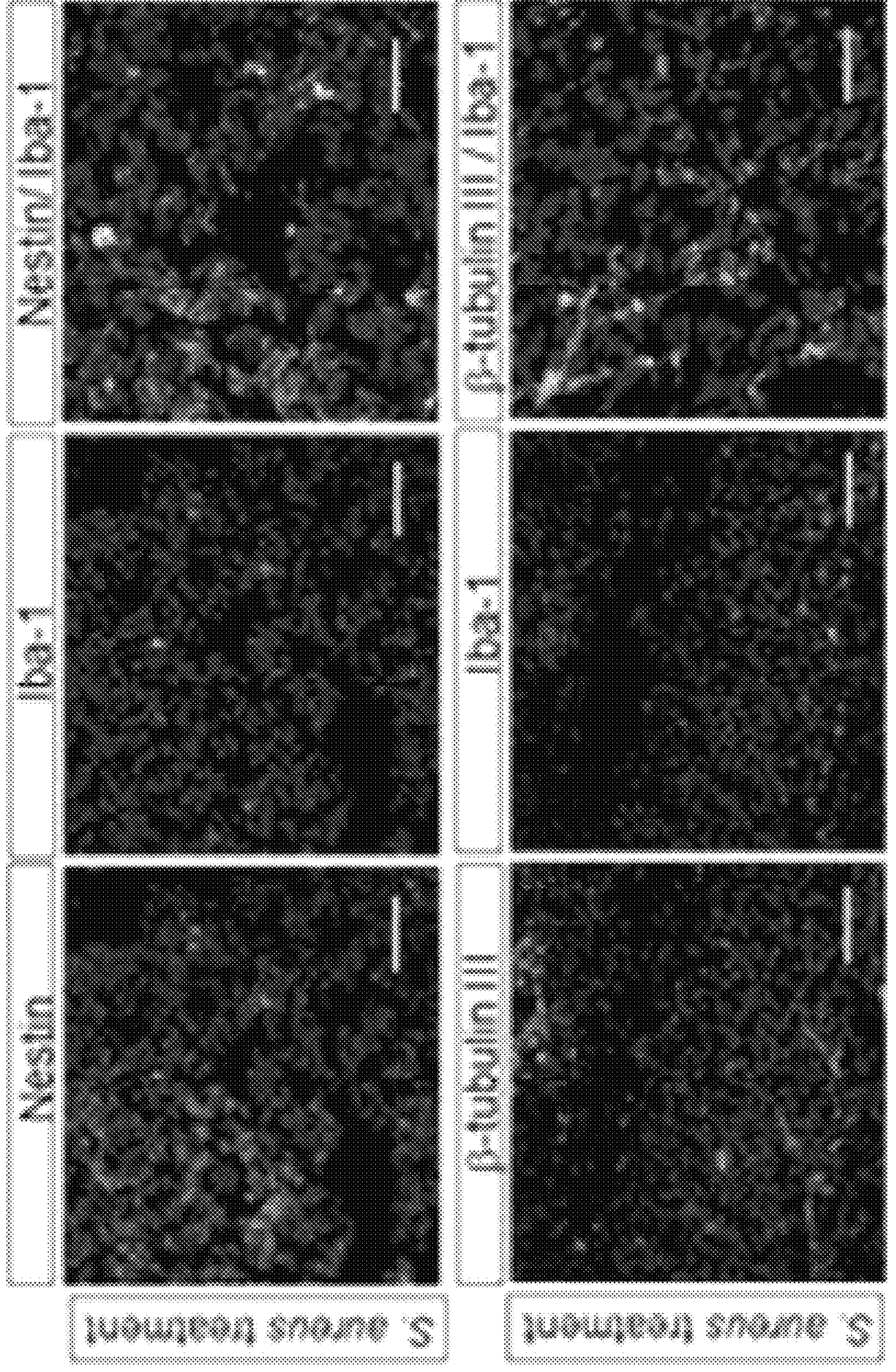
Figures 6, 6E:
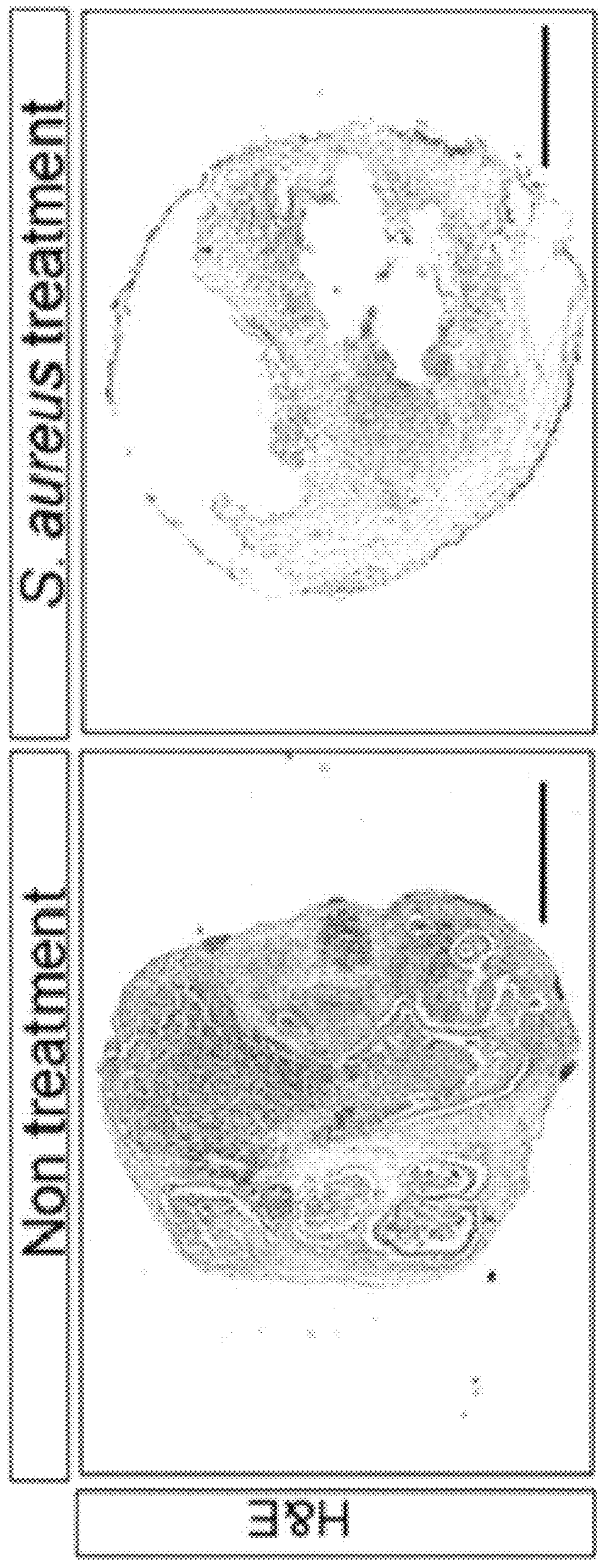
Figures 6, 6F:
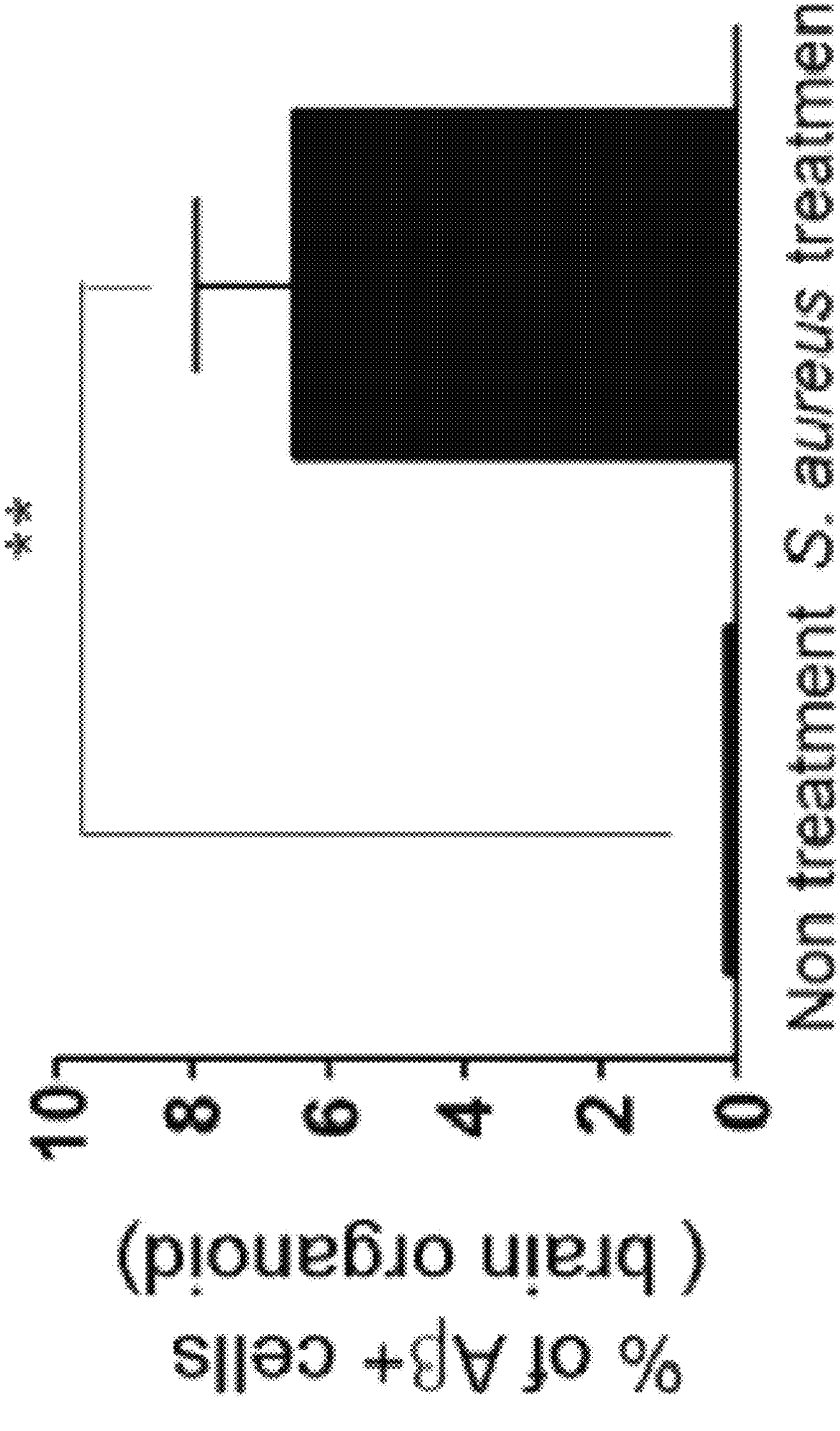

As shown in FIGS. 6A, 6B, and 6E, it was observed that the expression of beta amyloid protein increased in organoids treated with *Staphylococcus aureus* strains when compared to normal brain organoids, and that the beta amyloid protein and *Staphylococcus* strains were co-expressed.

In addition, as shown in FIGS. 6C and 6D, it was identified that the expression of Nestin and β-tubulin III, which are nerve cell-related markers, was reduced in organoids treated with *Staphylococcus aureus* strains when compared to normal brain organoids, and that the expression of Iba-1, which is an inflammatory cell marker, was increased.

In addition, as shown in FIG. 6E, it was identified that the organoids treated with bacteria were significantly deformed compared to normal organoids.

Example 7. Identification of Expression of Beta Amyloid, an Alzheimer's Disease-Inducing Factor, that is Increased in Concentration-Dependent Manner in *Staphylococcus Aureus* (*S. aureus*)

In the same manner as in Example 6, the brain organoid culture medium prepared using human dedifferentiated stem cells was treated with *Staphylococcus aureus* strains isolated from a patient at a concentration of 10 or 100 MOI for 2 to 3 hours, and H&E staining and immunofluorescence staining were analyzed. The H&E staining and immunofluorescence staining methods were the same as those of the aforementioned examples.

Figure 7:
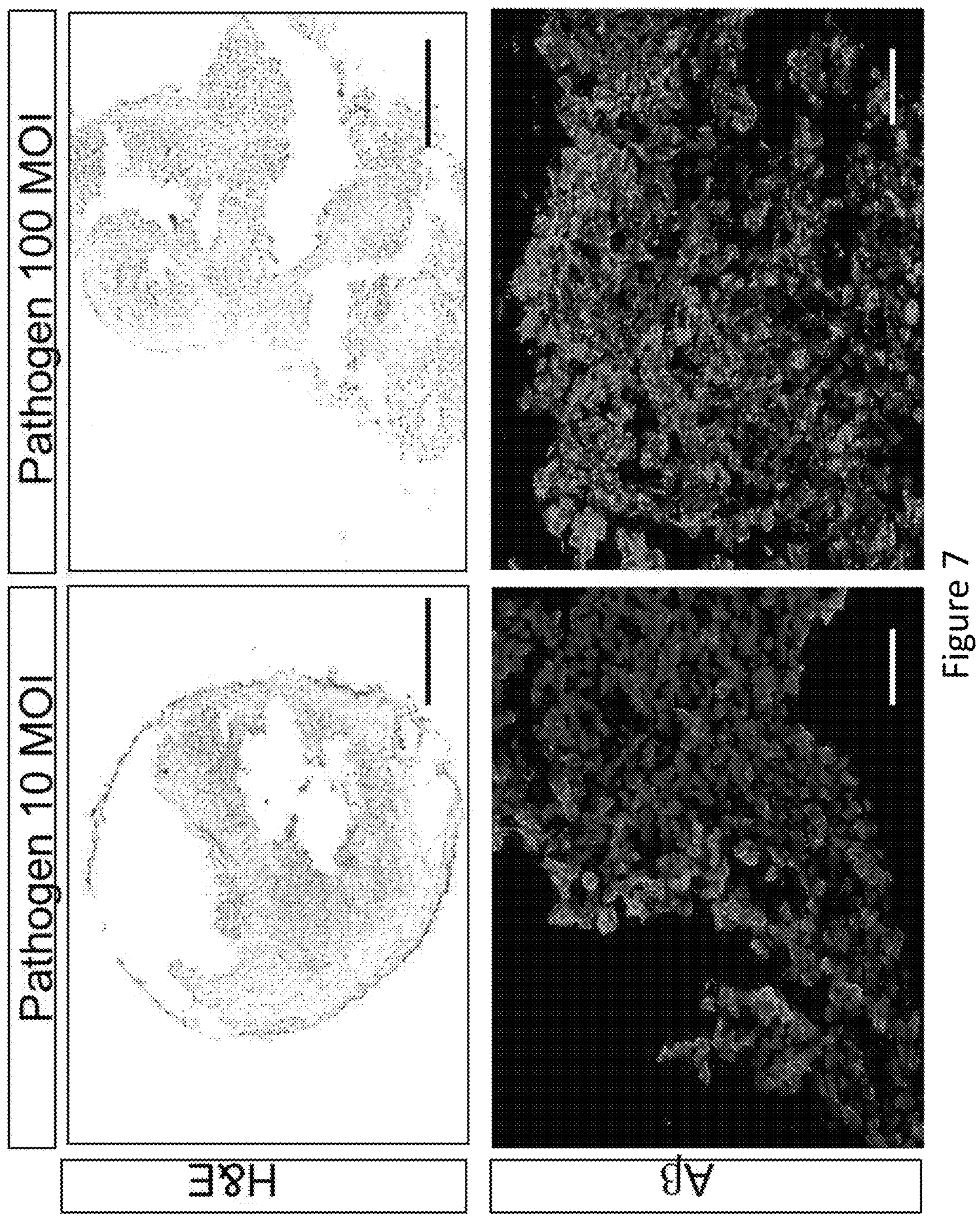
FIG. 7 is a result of performing H&E staining and immunofluorescence staining on human dedifferentiated stem cell-based brain organoids according to the treatment concentration of *Staphylococcus aureus* strains (10 MOI or 100 MOI), and identifies the H & E staining results and the expression of beta amyloid. The upper scale bar represents 500 μm and the lower scale bar represents 50 μm.

As a result, as shown in FIG. 7, it was identified that the form of the organoids in organoids treated with a concentration of 100 MOI of *Staphylococcus aureus* strains were deformed more than that of brain organoids treated with a concentration of 10 MOI of *Staphylococcus aureus* strains. In addition, it was observed that the expression of beta amyloid protein was increased.

Based on the above results, it was clearly identified that *Staphylococcus aureus* strains present in the palatine tonsil infected the actual brain and caused Alzheimer's disease.

In other words, as a result of the inflammatory reaction caused by *Staphylococcus aureus*, a pathogen present in large quantities in the palatine tonsils, accumulation of beta amyloid occurs in the palatine tonsils, and it is determined that Alzheimer's disease occurs due to the accumulation of beta amyloid.

Accordingly, according to an embodiment of the present disclosure, it is possible to prevent degenerative brain diseases that may occur in the aging process in advance through tonsillectomy, which converts the size of the tonsils of children born with enlarged tonsils to the original structure that is flat on the pharyngeal mucosa. It is expected that tonsillectomy may be used in adults and the elderly in the sense of removing the reservoir of pathogens.

The above description of the present disclosure is provided for the purpose of illustration, and it would be understood by those skilled in the technical field to which the present disclosure pertains that the present disclosure may be embodied in other specific forms without changing technical ideas or essential features of the present disclosure. Thus, it is clear that the above-described embodiments are illustrative in all aspects and do not limit the present disclosure.

INDUSTRIAL APPLICABILITY

The present disclosure can diagnose Alzheimer's disease through the expression of beta amyloid and/or *Staphylococcus aureus* in a palatine tonsil tissue and, furthermore, can be very advantageously used for revealing the pathogenesis of Alzheimer's disease and for treating Alzheimer's disease. Accordingly, the present disclosure has industrial applicability.

The invention claimed is:

1. A method for determining and treating a subject with Alzheimer's disease, the method comprising:

a) measuring an expression level or beta amyloid plaque accumulation level of beta amyloid in a tonsillar sample derived from a subject;

b) determining that the higher the expression level or beta amyloid plaque accumulation level of beta amyloid in the step a) is compared to an expression amount of normal people, the higher the risk of developing Alzheimer's disease; and c) performing a tonsillectomy on the subject determined in step b); and wherein the beta amyloid in step a) colocalizes with *Staphylococcus aureus*.

2. The method of claim 1, wherein a method for measuring the expression level is one or more selected from the group consisting of Western blotting, an ELISA, a radioimmunoassay, radioimmunodiffusion, Ouchterlony immunodiffusion, rocket immunoelectrophoresis, immunohistostaining, an immunoprecipitation assay, a complement fixation assay, FACS, and a protein chip assay.

3. The method of claim 1, wherein the step a) further comprises measuring an expression level of *Staphylococcus aureus* strains.

4. The method of claim 1, wherein the subject is a patient with a tonsil-related disease.

5. The method of claim 4, wherein the tonsil-related disease is tonsillitis or enlarged tonsils.

6. The method of claim 1, wherein the tonsillar sample is tonsil tissue or tonsillar stone.

7. A method for determining and treating patients subject to tonsillectomy, the method comprising:

a) measuring an expression level or beta amyloid plaque accumulation level of beta amyloid in a tonsillar sample derived from a subject;

b) determining that the higher the expression level or beta amyloid plaque accumulation level of beta amyloid in the step a) is compared to an expression amount of normal people, the subject is determined to be a subject for tonsillectomy; and c) performing a tonsillectomy on the subject determined in step b).

8. The method of claim 7, wherein the step a) further comprises measuring an expression level of *Staphylococcus aureus* strains.

9. The method of claim 7, wherein the subject is a patient with a tonsil-related disease.

10. A method for determining and treating a subject with Alzheimer's disease, the method comprising:

a) measuring an expression level of *Staphylococcus aureus* strains in a tonsillar sample obtained from a subject;

b) determining that the higher the expression level of *Staphylococcus aureus* in the step a) is compared to an expression amount of normal people, the higher the risk of developing the Alzheimer's disease; and c) performing a tonsillectomy on the subject determined in step b).

* * * * *